United States Patent
Yi et al.

(10) Patent No.: US 7,595,413 B2
(45) Date of Patent: Sep. 29, 2009

(54) PHOSPHINE-SUBSTITUTED VINYL CONTAINING METALLOCENE CATALYST, PREPARATION PROCESS AND THE APPLICATION OF THE SAME

(75) Inventors: Jianjun Yi, Beijing (CN); Wenhua Sun, Beijing (CN); Peng Hao, Beijing (CN); Shu Zhang, Beijing (CN)

(73) Assignee: PetroChina Company Limited, Beijing (CN)

( * ) Notice: Subject to any disclaimer, the term of this patent is extended or adjusted under 35 U.S.C. 154(b) by 0 days.

(21) Appl. No.: 12/068,662

(22) Filed: Feb. 8, 2008

(65) Prior Publication Data

US 2008/0194854 A1 Aug. 14, 2008

(30) Foreign Application Priority Data

Feb. 14, 2007 (CN) .......................... 2007 1 0063909

(51) Int. Cl.
*C07F 17/00* (2006.01)
*B01J 31/00* (2006.01)
*C07F 7/00* (2006.01)
*C08F 4/44* (2006.01)

(52) U.S. Cl. .......................... 556/22; 556/52; 526/145; 502/103; 502/117

(58) Field of Classification Search ................. 556/22, 556/52; 502/103, 117; 526/145
See application file for complete search history.

(56) References Cited

OTHER PUBLICATIONS

Breen et al., Organometallics, vol. 15, No. 26, pp. 5729-5737 (1996).*
Xi et al., Organometallics, vol. 26, No. 4, pp. 1084-1088 (publication date (Web); Jan. 20, 2007).*

* cited by examiner

*Primary Examiner*—Porfirio Nazario Gonzalez
(74) *Attorney, Agent, or Firm*—Morrison & Foerster LLP

(57) ABSTRACT

The invention relates to a phosphine-substituted vinyl containing metallocene catalyst, and also to the preparation process of the same as well as to the application of the catalyst. The catalyst has the general formula of $Cp_2(CR^1=CR^2(P(R^3)_2))MX$, wherein Cp is a ligand containing cyclopentadiene having 1~5 substitutions, of which two neighbors connecting to each other to form fused rings having more than two members; $R^1$-$R^3$ is selected from the groups consisting of hydrogen, $C_1$~$C_{18}$ alkyl or perfluoro-alkyl, $C_6$~$C_{24}$ aralkyl or alkaryl; M is selected from the groups consisting of metals of the IVB group; and X is selected from the groups consisting of halogens, $C_1$~$C_{24}$ alkyl alkoxyl, silicone or alkaryl. With aluminoxane or modified aluminoxane, aluminum alkyl, halogenated aluminum alkyl or their mixture as the catalyst promoter the phosphine-substituted vinyl containing metallocene catalyst may be employed as the major catalyst for the polymerization or copolymerization of alpha-olefin. Due to its high activity, the polymerization may occur at both high and low temperatures with the polymer having higher molecular weight and broader molecular weight distribution.

26 Claims, No Drawings

PHOSPHINE-SUBSTITUTED VINYL CONTAINING METALLOCENE CATALYST, PREPARATION PROCESS AND THE APPLICATION OF THE SAME

FIELD OF THE INVENTION

The invention relates to a phosphine-substituted vinyl containing metallocene catalyst, and also to the process for preparation of the same and its application in the polymerization or copolymerization of olefin.

BACKGROUND OF THE INVENTION

In 1980, Sinn et. al. found that with MAO as the cocatalyst, $Cp_2ZrMe_2$ exhibited remarkable ability for the polymerization of olefin, thereby raising the upsurge of studies on metallocene catalysts, which, in the catalysis of ethylene polymerization, show high activity, favorable copolymerizing performance and narrow molecular weight distribution of polymers etc. Metallocene catalysts having Cs or Cl symmetry may catalyze the polymerization of propylene to obtain structure-controllable polypropylene (Angew. Chem. Int. Ed. Engl., 1995, 34, 1143; EP 37130 (1993); CA 119, 2507262 (1993)). In the late of 1980s, a bridge hydrazine-cyclopentadienyl ligand containing constrained geometry configurated semi-metallocene catalyst (CGC catalyst) was invented, which manifested exceedingly high activity in the catalysis of polymerization of propylene as well as copolymerization of ethylene and alpha-olefin (EP 416815 (1991); EP 420436 (1991); Chem. Rev., 2003, 103, 283.). In recent years, polyolefin catalysts having large p bond ligands have been rapidly developed. Other than typical transition metal complexes with cyclopentadiene and its derivatives as ligands, the application of another category of transition metal complexes containing coordinated heteroatom ligands such as oxygen, nitrogen etc. for the catalysis of olefin polymerization has been paid more and more attention to. For instance, U.S. Pat. No. 5,539,124 discloses a pyrrole ring containing transition metal catalyst, whose general formula is expressed as (L)m (Cp)qM(Y)n(B)p, wherein L is a ligand or mixture of ligands, one of which containing at least two fused rings with one being pyrrole ring; Cp is a group containing cyclopentadiene; two L ligands or one L and Cp may be bonded into a bridge; B is Lewis base; Y is selected from the groups consisting of halogens, $C_1~C_{20}$ alkoxyl, $C_1~C_{20}$ silicone, $N(R_1)_2$ or a mixture thereof, M is Ti or Zr; m is 1~4, n is 0~2, p is 0~2, q is 0~1 and m+n+q=4. The catalyst can be used to catalyze the polymerization of olefin, but has low catalytic activity. For instance, if MAO was as cocatalyst, dipyrrole zirconium dichloride had the catalytic activity only for 1.5 kg polyethylene/molar catalyst/hour under 1.0 MPa at 110° C. CN1169736A discloses a olefin polymerizing catalyst having the general formula of $CpML_m{}^1Y_{3-m}$, wherein Cp is a group having cyclopentadienyl bone; M is Ti, Zr or Hf; $L^1$ represents a negative monovalent bidentate anion ligand in which the $X^1$, $X^2$ and N bonded on C atom are ligating atoms respectively with $X^1$ being O, S, Se or Te and $X^2$ being S, Se or Te; Y represents halogen atoms, $C_1~C_{20}$ alkoxyl or $C_1~C_{20}$ hydrocarbonyl-substituted amino etc; m is 1, 2 or 3. The catalytic system is investigated by adopting a series of negative monovalent bidentate anion ligands and demonstrated fairly high activity. CN 1151993A discloses a novel metallocene catalyst for the polymerization of ethylene, which adopts pyrrolyl or its derivatives as coordinate ligands, and exhibits high catalytic activity in combination with sesquiethyl. The produced polyethylene performed low molecular weight and narrow molecular weight distribution. For instance, at the reaction temperature of 50oC, under the ethylene pressure of 0.04 MPa, after 7 hours' reaction, dipyrrole titanium dichloride has the polymerization activity of $3.4\times10^5$ g polyethylene/molar titanium/hour, and the molecular weight distribution of the polyethylene is 1.47.

SUMMARY OF THE INVENTION

The object of the invention is to provide a phosphine-substituted vinyl containing metallocene catalyst with highly catalytical activity, and also the preparation process of the same as well as its application.

Said phosphine-substituted vinyl containing metallocene catalyst of the invention has the general formula of $Cp_2(CR^1=CR^2(P(R^3)_2))MX$ and the general formula of

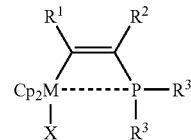

wherein Cp is a ligand containing cyclopentadiene having 1~5 substitutions, of which two neighbors connecting to each other to form fused rings having more than two members; $R^1$-$R^3$ is selected from the groups consisting of hydrogen, $C_1~C_{18}$ alkyl or perfluoro-alkyl, $C_6~C_{24}$ aralkyl or alkaryl; M is selected from the groups consisting of metals of IVB group; X is selected from the groups consisting of halogens, $C_1~C_{24}$ alkyl alkoxyl, silicone or alkaryl;

In formula, M is selected from the groups consisting of titanium, zirconium or celtium; X is selected from the groups consisting of halogens, $C_1~C_6$ alkyl, alkoxyl, silicone or benzyl. Preferably, M is titanium or zirconium; Preferably, X is halogen or benzyl.

$R^1$ and $R^2$ are respectively selected from the groups consisting of hydrogen, $C_1~C_6$ alkyl, $C_1~C_6$ perfluoro-alkyl, $C_6~C_{24}$ aralkyl or alkaryl, preferably ethyl, propyl, butyl, phenyl or para-methyl phenyl; $R^3$ is selected from the groups consisting of phenyl, methyl, isopropyl or cyclohexyl.

Preferably, said Cp is mono- or poly-substituted groups by cyclopentadienyl, indenyl or flourenyl; for the present invention, preferably, $R^1$-$R^3$ in the structure formula of phosphine-substituted vinyl metallic complex is $C_1~C_{18}$ alkyl or perfluoro-alkyl. Exemplarily, to the following combinations, the corresponding preferable metallic complex is 1-31:

1: $R^1$=Et, $R^2$=Et, $R^3$=Ph;
2: $R^1$=Et, $R^2$=Ph, $R^3$=Ph;
3: $R^1$=Ph, $R^2$=Et, $R^3$=Ph;
4: $R^1$=Pr, $R^2$=Pr, $R^3$=Ph;
5: $R^1$=Bu, $R^2$=Bu, $R^3$=Ph;
6: $R^1$=Ph, $R^2$=Ph, $R^3$=Ph;
7: $R^1$=p-Tol, $R^2$=p-Tol, $R^3$=Ph;
8: $R^1$=Et, $R^2$=Et, $R^3$=Me;
9: $R^1$=Et, $R^2$=Ph, $R^3$=Me;
10: $R^1$=Ph, $R^2$=Et, $R^3$=Me;
11: $R^1$=Pr, $R^2$=Pr, $R^3$=Me;
12: $R^1$=Bu, $R^2$=Bu, $R^3$=Me;
13: $R^1$=Ph, $R^2$=Ph, $R^3$=Me;
14: $R^1$=p-Tol, $R^2$=p-Tol, $R^3$=Me;
15: $R^1$=Et, $R^2$=Et, $R^3$=i-Pr;
16: $R^1$=Et, $R^2$=Ph, $R^3$=i-Pr;
17: $R^1$=Ph, $R^2$=Et, $R^3$=i-Pr;
18: $R^1$=Pr, $R^2$=Pr, $R^3$=i-Pr;

19: $R^1$=Bu, $R^2$=Bu, $R^3$=i-Pr;
20: $R^1$=Ph, $R^2$=Ph, $R^3$=i-Pr;
21: $R^1$=p-Tol, $R^2$=p-Tol, $R^3$=i-Pr;
22: $R^1$=Et, $R^2$=Et, $R^3$=Cy;
23: $R^1$=Et, $R^2$=Ph, $R^3$=Cy;
24: $R^1$=Ph, $R^2$=Et, $R^3$=Cy;
25: $R^1$=Pr, $R^2$=Pr, $R^3$=Cy;
26: $R^1$=Bu, $R^2$=Bu, $R^3$=Cy;
27: $R^1$=Ph, $R^2$=Ph, $R^3$=Cy;
28: $R^1$=p-Tol, $R^2$=p-Tol, $R^3$=Cy;
29: $R^1$=Ph, $R^2$=Ph, $R^3$=Ph;
30: $R^1$=Bu, $R^2$=Bu, $R^3$=Ph;
31: $R^1$=Ph, $R^2$=Ph, $R^3$=Ph;
1-28 (M=Zr); 29-30 (M=Ti); 31 (M=Hf)

The process for the preparation of the catalyst of the invention comprises the steps of (1) Adding a dihalide dicyclopentadienyl metallic compound into a solvent and then a first strong alkaline compound to form a first mixture; wherein the amount of the solvent is 10~20 times the weight of the dihalide dicyclopentadienyl metallic compound; the first strong alkaline compound and the dihalide dicyclopentadienyl metallic compound are in the proportion of 1.2:2 by weight;

(2) Adding a second alkaline compound into the first mixture and then alkyne compound to form a second mixture; wherein the alkyne compound, the first and second alkaline compounds, and the dihalide dicyclopentadienyl metallic compound are in the proportion of 1:2:1.2 by weight;

(3) Adding dialkyl phosphorus halide and then 3M dilute hydrochloric acid into the second mixture to get the coarse products; wherein the dialkyl phosphorus halide and the dihalide dicyclopentadienyl metallic compound are in the proportion of 1:1.2 by weight.

In a preferable embodiment, the specific process for the preparation of the catalyst of the invention is as follows:

(1) Under the protection of highly pure nitrogen gas, adding a dihalide biscyclopentadienyl metallic compound into the Schlenk reaction bottle, stirring uniformly within a solvent free of oxygen and water, adding a first strong alkaline compound and maintaining for 1 hour to form a first mixture; wherein the amount of the solvent is 10~20 times the weight of the dihalide dicyclopentadienyl metallic compound; the first strong alkaline compound and the dihalide dicyclopentadienyl metallic compound are in the proportion of 1.2:2 by weight;

(2) Adding a second alkaline compound into the first mixture and after reaction for 1 hour, adding alkyne compound and continuing the reaction for 1-3 hours to form a second mixture; wherein the alkyne compound, the first and second alkaline compounds, and the dihalide dicyclopentadienyl metallic compound are in the proportion of 1:2:1.2 by weight;

(3) Adding dialkyl phosphorus halide and after 1-3 hours' reaction, adding 3M dilute hydrochloric acid into the second mixture to form a third mixture, extracting the third mixture with organic solvent to obtain a filtrate, combining the filtrate and concentrating to get a coarse products; wherein the dialkyl phosphorus halide and the dihalide dicyclopentadienyl metallic compound are in the proportion of 1:1.2 by weight; the amount of the organic solvent is 10~20 times the total weight of the reactants.

(4) Separating the coarse products with a chromatographic column and eluants to get a white solid product, which characterized by element analysis, $^1$H NMR, $^{13}$C NMR and ESI-MS.

The metal in said dihalide dicyclopentadienyl metallic compound is titanium, zirconium or celtium.

The first strong alkaline compound in the process is selected from the groups consisting of alkylates or hydrides of alkali metals or alkyl magnesium bromide. For the alkylates, the alkali metal is preferably lithium, sodium or potassium, and the alkyl is preferably methyl, ethyl or butyl, e.g. butyl lithium; in alkyl magnesium halide, the alkyl is preferably $C_1$~$C_8$ alkyl or $C_6$~$C_{18}$ aralkyl e.g. methyl magnesium bromide, butyl magnesium bromide, benzyl magnesium bromide.

The solvent in said process is preferably diethyl ether or tetrahydrofuran.

The second alkaline compound in said process is tri-substituted organic amine or pyridines compounds, preferably N,N-dimethyl-4-methylaminopyridine (DMAP).

The alkyne compound is $C_2$~$C_{24}$ ethyne compound, 2-crotonylene, 3-hexyne, 4-octyne, 5-decyne, 1-phenyl allylene; 1-phenyl valerylene, 1,2-diphenylacetylene, 1,2-dinaphthylacetylene, 1,2-di(para-chlorophenyl)acetylene; 1,2-di(o-chlorophenyl) acetylene.

The general formula of said dialkyl phosphorus halide compound is $XPR_2$, wherein X is selected from the groups consisting of halogens, preferably Cl and Br; R is selected from the groups consisting of hydrocarbonyl, preferably derivatives of alkyl or aryl, or halogen-substituted derivatives of alkyl or aryl, e.g. methyl, trifluoro methyl, phenyl, benzyl, pentafluoro phenzyl;

The organic solvent in said process is halogenated hydrocarbon or aromatic hydrocarbon compounds, preferably dichloromethane, trichlormethane, toluene, chlorobenzene, dichloro-benzene and the like.

The stationary condition for chromatographic column is 100-500 mesh silica gel, preferably 150-350 mesh silica gel.

Said eluant is alkane or oxygen-containing organic solvent, or mixture of the both preferably pentane, hexane, tetrahydrofuran, petroleum ether/tetrahydrofuran mixed solvent.

The phosphine-substituted vinyl containing metallocene catalyst of the present invention is suitable for the homopolymerization or copolymerization of alpha-olefin monomers. The strong Lewis acidic compounds are used in the polymerization as the catalyst promoter, including aluminoxane or modified aluminoxane, aluminum alkyl, halogenated aluminum alkyl or their mixture; specifically, aluminoxian may be linear or annular polymers; preferably, aluminoxane is methyl aluminoxane (MAO), ethyl aluminoxane or isobutyl aluminoxane; alkyl aluminum is trimethyl aluminum, triethyl aluminum, triisobutyl aluminum or triorthohexyl aluminum; halogenated alkyl aluminum is diethyl aluminium chloride, sesquiethyl aluminum chloride or ethyl aluminium dichloride; their mixture includes the mixture of methyl aluminoxane and aluminum alkyl (e.g. MMAO etc.).

The polymerization conditions include: the molar ratio of the metallicum alumina in the catalyst precursor and the central metal in the major catalyst (Al/M) being 10~50000, the temperature of polymerization being 0~150° C., and the pressure of polymerization being 0.01~10.0 MPa; preferably, the molar ratio (Al/M) being 200~20000, the temperature of polymerization being 20~120° C., and the pressure of polymerization being 0.1~5.0 MPa.

In the phosphine-substituted vinyl catalytic system of the invention, alpha-olefin monomer which can be catalyzed is preferably $C_2$~$C_{24}$ olefin, including ethylene, propylene, 1-butene, 1-hexene, 1-caprene, 1-decene, 1-dodecene, 1-tetradecene, norborene, styrene or mixture of any two of them. Alpha-olefin monomers which can be copolymerized with ethylene include propylene, 1-butylene, 1-hexylene, 1-caprylene, 1-decylene, 1-dodecylene, 1-tetradecene, norborene, styrene or mixture of any two of them.

The polymerization process of the invention can be solution polymerization, e.g. slurry polymerization, in which the solvent for polymerization may be organic solvents including alkane, arene or halogenated hydrocarbon and the like; or be gas phase bulk polymerization with the catalyst of the invention to produce olefin polymers.

The phosphine-substituted vinyl IVB group metallic olefin polymerizing catalyst of the invention is a phosphine-substituted vinyl dicyclopentadienyl ligand containing halogenated IVB group metallic complex, wherein the IVB group metal coordinates with two cyclopentadienyls or their derivative ligands in cis-form, and the single halogen ligand coordinates with the phosphine-substituted vinyl ligand in cis-form. The catalyst of the invention has fairly high activity when applied for the polymerization or copolymerization of alpha-olefin. The polymerization may carry out at both low and high temperatures; and the resulting polymers have high molecular weight and broad molecular weight distribution.

DETAILED DESCRIPTION OF THE PREFERRED EMBODIMENTS

The following examples are included for illustrative purposes only and not intended to limit the scope of the invention.

In the examples, the preparations of catalyst are all conducted with Schlenk equipment under the protection of high purity nitrogen gas. In the examples, Cp, Ind and Flu represented cylopentadienyl, indenyl and fluorenyl respectively. The examples are shown as following.

EXAMPLE 1

Preparation for Dicylopentadienyl (1,2-diethyl-vinyl diphenylphosphine) zirconium chloride [1: $Cp_2(C(C_2H_5)=C(C_2H_5)P(C_6H_5)_2)ZrCl$]

(1) Under the protection of highly pure nitrogen gas, 1.2 mmol dichloro-zirconocene and 5 ml tetrahydrofuran solvent treated by freedom of oxygen and water were added into a 20 ml Schlenk reaction tube and stirred uniformly to form a first mixture; the first mixture was cooled to −78° C. with dry ice-acetone bath or liquid nitrogen-acetone bath; and then 2.4 mmol n-butyl lithium solution was added into the first mixture and kept for 30 min to form a second mixture.
(2) N,N-dimethyl-4-methylaminopyridine (DMAP) (2.0 mmol) was added into the second mixture and reacted at room temperature for 1 hour to form a third mixture; 3-hexyne (1.0 mmol) was added into the third mixture and stirred continuously for 1 hour; and then ClPPh$_2$ (1.0 mmol) was add into and stirred for 1 hour at this temperature to form a fourth mixture.
(3) 2 ml dilute hydrochloric acid (3M) was added into the fourth mixture to form a product; the product was extracted with 30 ml dichloromethane three times to form the filtrates; the filtrates were combined and concentrated by rotary evaporation to obtain the coarse products.
(4) The coarse products were column-separated (300 mesh silica gel) with petroleum ether/tetrahydrofuran (10/1) as the eluant to obtain 215 mg white solid dicyclopentadienyl (1,2-diethyl-vinyl diphenylphosphine) zirconium chlorinate [1: $Cp_2(C(C_2H_5)=C(C_2H_5)P(C_6H_5)_2)ZrCl$] with the isolated yield of 65%. The theoretical values (%) and experimental values (%) of the element analysis ($C_{28}H_{30}ClPZr$) were respectively C, 64.16; H, 5.77; Cl, 6.76; P, 5.91 and C, 64.03; H, 6.03, Cl, 6.51; P, 5.77.

EXAMPLE 2

Preparation for Dicylopentadienyl (1-phenyl-2-ethyl-vinyl diphenylphosphine) zirconium chloride [2: $Cp_2(C(C_2H_5)=C(C_6H_5)P(C_6H_5)_2)ZrCl$]

The experimental procedures were the same as those of Example 1, except that the alkyne was substituted to 1-phenyl-1-crotonylene (1.0 mmol). After separation, 229 mg while solid dicylopentadienyl (1-phenyl-2-ethyl-vinyl diphenylphosphine) zirconium chloride [2: $Cp_2(C(C_2H_5)=C(C_6H_5)P(C_6H_5)_2)ZrCl$] was obtained with the isolated yield of 40%. Following are the compound's data of NMR and element analysis: $^1$H NMR (300 MHz, CDCl$_3$, Me$_4$Si) d 0.98 (t, J=7.2 Hz, 3H), 2.60 (m, J=3.78 Hz, $^4J_{PH}$=15.1 Hz, 2H), 6.00 (s, 10H), 7.08-7.11 (m, 2H), 7.20-7.23 (m, 3H), 7.32-7.34 (m, 6H), 7.57-7.62 (m, 4H); $^{13}$C NMR (75 MHz, CDCl$_3$, Me$_4$Si) d 14.4, 32.4 (d, $^3J_{PC}$=35.9 Hz), 110.1, 126.5, 128.0 (d, $^3J_{PC}$=2.2 Hz), 128.4 (d, $^3J_{PC}$=7.9 Hz), 128.4, 129.5, 133.3 (d, $^2J_{PC}$=10.0 Hz, 4C), 134.2 (d, $^1J_{PC}$=17.9 Hz), 138.3 (d, $^1J_{PC}$=39.4 Hz), 139.9 (d, $^2J_{PC}$=3.6 Hz), 220.3 (d, $^2J_{PC}$=16.5 Hz); $^{31}$P NMR (81 MHz, CDCl$_3$, 85% H$_3$PO$_4$) d -39.4; Positive ion ESI-MS: 535.0 (M$^+$); element analysis: ($C_{32}H_{30}ClPZr$) theoretical values (%): C 67.17, H, 5.28, Cl 6.20, P, 5.41. experimental values (%): C 67.29, H 5.58, Cl 5.98, P 5.27.

EXAMPLE 3

Preparation for Dicylopentadienyl (1-ethyl-2-phenyl-vinyl diphenylphosphine) zirconium chloride [3: $Cp_2(C(C_6H_5)=C(C_2H_5)P(C_6H_5)_2)ZrCl$]

The experimental procedures were the same as those of Example 1, except that the alkyne was substituted to 1-phenyl-1-crotonylene (1.0 mmol). After separation, 114 mg while solid dicylopentadienyl (1-ethyl-2-phenyl-vinyl diphenylphosphine) zirconium chloride [3: $Cp_2(C(C_6H_5)=C(C_2H_5)P(C_6H_5)_2)ZrCl$] was obtained with the isolated yield of 20%. Following are the compound's data of NMR and element analysis: $^1$H NMR (300 MHz, CDCl$_3$, Me$_4$Si) d 0.63 (t, J=7.5 Hz, 3H), 2.22-2.29 (m, J=7.5 Hz, $^3J_{PH}$=2.4 Hz, 2H), 5.91 (s, 10H), 7.16-7.26 (m, 2H), 7.34-7.38 (m, 3H), 7.41-7.45 (m, 6H), 7.69-7.75 (m, 4H); $^{13}$C NMR (75 MHz, CDCl$_3$, Me$_4$Si) d 14.8, 25.7 (d, $^2J_{PC}$=4.3 Hz), 111.1, 123.9, 124.5, 125.6, 128.7 (d, $^3J_{PC}$=8.6 Hz), 129.7, 133.1 (d, $^2J_{PC}$=10.8 Hz), 134.1 (d, $^1J_{PC}$=18.6 Hz), 141.2 (d, $^1J_{PC}$=37.3 Hz), 150.5 (d, $^3J_{PC}$=39.4 Hz), 221.2 (d, $^2J_{PC}$=24.4 Hz); $^{31}$P NMR (81 MHz, CDCl$_3$, 85% H$_3$PO$_4$) d -40.2; Positive ion ESI-MS: 535.0 (M$^+$); element analysis: ($C_{32}H_{30}ClPZr$) theoretical values (%): C, 67.17; H, 5.28; Cl, 6.20; P, 5.41; experimental values (%): C 67.47, H 5.44, Cl 6.08, P 5.07.

EXAMPLE 4

Preparation for Dicylopentadienyl-1,2-dipropyl-vinyl diphenylphosphine zirconium chloride [4: $Cp_2(C(C_3H_7)=C(C_3H_7)P(C_6H_5)_2)ZrCl$]

The experimental procedures were the same as those of Example 1, except that the alkyne was substituted to 4-octyne (1.0 mmol). After separation, 390 mg while solid Dicylopentadienyl-1,2-dipropyl-vinyl diphenylphosphine zirconium chloride [4: $Cp_2(C(C_3H_7)=C(C_3H_7)P(C_6H_5)_2)ZrCl$] was obtained with the isolated yield of 71%. Following are the compound's data of NMR and element analysis: $^1$H NMR (300 MHz, CDCl$_3$, Me$_4$Si) d 0.73 (t, $^3J_{HH}$=7.2 Hz, 3H), 0.85 (m, 2H), 1.07 (t, $^3J_{HH}$=7.5 Hz, 3H), 1.66-1.74 (m, 2H), 2.25-2.40 (m, 4H), 5.90 (s, 10H), 7.37 (m, 6H), 7.56-7.62 (m, 4H); $^{13}$C NMR (75 MHz, CDCl$_3$, Me$_4$Si) d 14.5, 15.7, 22.4, 24.0, 34.0 (d, $^2J_{PC}$=3.6 Hz), 42.4 (d, $^3J_{PC}$=37.3 Hz), 110.1, 128.5 (d, $^3J_{PC}$=7.9 Hz), 129.4, 133.3 (d, $^2J_{PC}$=10.5 Hz), 135.0 (d, $^1J_{PC}$=18.6 Hz), 138.8 (d, $^1J_{PC}$=40.2 Hz), 214.1 (d, $^2J_{PC}$=15.1 Hz); $^{31}$P NMR (81 MHz, CDCl$_3$, 85% H$_3$PO$_4$) d - 44.2; Positive ion ESI-MS: 515.0 (M$^+$); element analysis (C$_{30}$H$_{34}$ClPZr) theoretical values (%): C 65.25, H 6.21, Cl 6.42, P 5.61; experimental values (%): C 65.03, H 6.38, Cl 6.27, P 5.53.

EXAMPLE 5

Preparation for Dicylopentadienyl (1,2-dibutyl-vinyl diphenylphosphine) zirconium chloride [5: Cp$_2$(C(C$_4$H$_9$)=C(C$_4$H$_9$)P(C$_6$H$_5$)$_2$)ZrCl]

The experimental procedures were the same as those of Example 1, except that the alkyne was substituted to 5-decyne (1.0 mmol). After separation, 439 mg while solid Dicylopentadienyl (1,2-dibutyl-vinyl diphenylphosphine) zirconium chloride [5: Cp$_2$(C(C$_4$H$_9$)=C(C$_4$H$_9$)P(C$_6$H$_5$)$_2$)ZrCl] was obtained with the isolated yield of 76%. Following are the compound's data of NMR and element analysis: $^1$H NMR (300 MHz, CDCl$_3$, Me$_4$Si) d 0.72 (t, $^3J_{HH}$=7.2 Hz, 3H), 1.03 (t, $^3J_{HH}$=7.2 Hz, 3H), 1.11-1.18 (m, 2H), 1.28-1.35 (m, 2H), 1.43-1.51 (m, 2H), 1.62-1.72 (m, 2H), 2.28-2.42 (m, 4H), 5.90 (s, 10H), 7.37 (m, 6H), 7.56-7.62 (m, 4H); $^{13}$C NMR (75 MHz, CDCl$_3$, Me$_4$Si) d 13.8, 14.2, 23.0, 24.2, 31.1, 31.4 (d, $^2J_{PC}$=3.6 Hz), 32.8, 39.6 (d, $^3J_{PC}$=37.3 Hz), 110.1, 128.4 (d, $^3J_{PC}$=7.9 Hz), 129.4, 133.3 (d, $^2J_{PC}$=10.8 Hz), 135.0 (d, $^1J_{PC}$=17.9 Hz), 138.8 (d, $^1J_{PC}$=38.7 Hz), 214.1 (d, $^2J_{PC}$=15.1 Hz); $^{31}$P NMR (81 MHz, CDCl$_3$, 85% H$_3$PO$_4$) d - 44.2; Positive ion ESI-MS: 543.0 (M$^+$); element analysis (C$_{32}$H$_{38}$ClPZr) theoretical values (%): C 66.23, H, 6.60, Cl 6.11, P 5.34: experimental values (%): C 66.01, H 6.51, Cl 5.94, P 5.09.

EXAMPLE 6

Preparation for Dicylopentadienyl (1,2-diphenyl-vinyl diphenylphosphine) zirconium chloride [6: Cp$_2$(C(C$_6$H$_5$)=C(C$_6$H$_5$)P(C$_6$H$_5$)$_2$)ZrCl]

The experimental procedures were the same as those of Example 1, except that the alkyne was substituted to diphenyl ethyne (1.0 mmol). After separation, 539 mg while solid Dicylopentadienyl (1,2-diphenyl-vinyl diphenylphosphine) zirconium chloride [6: Cp$_2$(C(C$_6$H$_5$)=C(C$_6$H$_5$)P(C$_6$H$_5$)$_2$)ZrCl] was obtained with the isolated yield of 87%. Following are the compound's data of NMR and element analysis: $^1$H NMR (300 MHz, CDCl$_3$, Me$_4$Si) d 5.91 (s, 10H), 6.81-6.84 (m, 2H), 6.96-7.12 (m, 6H), 7.26-7.31 (m, 2H), 7.40-7.42 (m, 6H), 7.73-7.79 (m, 4H); $^{13}$C NMR (75 MHz, CDCl$_3$, Me$_4$Si) d 111.2, 124.9, 125.0, 126.3, 127.8, 128.5, 128.7 (d, $^3J_{PC}$=7.5 Hz), 129.1 (d, $^3J_{PC}$=3.0 Hz), 129.7, 132.8 (d, $^2J_{PC}$=9.8 Hz), 133.2 (d, $^1J_{PC}$=18.6 Hz), 137.8 (d, $^1J_{PC}$=38.7 Hz), 138.0 (d, $^2J_{PC}$=2.9 Hz), 150.4 (d, $^3J_{PC}$=38.7 Hz), 215.0 (d, $^2J_{PC}$=21.5 Hz); $^{31}$P NMR (81 MHz, CDCl$_3$, 85% H$_3$PO$_4$) d-38.3; Positive ion ESI-MS: 583.0 (M$^+$); element analysis (C$_{36}$H$_{30}$ClPZr) theoretical values (%): C 69.71, H 4.87, Cl 5.72, P 4.99; experimental values (%): C 69.59, H 4.99, Cl 5.57, P 5.21.

EXAMPLE 7

Preparation for Dicylopentadienyl (1,2-di(4-methylphenyl)-vinyl diphenylphosphine) zirconium chloride [7: Cp$_2$(C(CH$_3$C$_6$H$_5$)=C(CH$_3$C$_6$H$_5$)P(C$_6$H$_5$)$_2$)ZrCl]

The experimental procedures were the same as those of Example 1, except that the alkyne was substituted to di(4-methylphenyl)-ethyne (1.0 mmol). After separation, 550 mg while solid Dicylopentadienyl (1,2-di(4-methylphenyl)-vinyl diphenylphosphine) zirconium chloride [7: Cp$_2$(C(CH$_3$C$_6$H$_5$)=C(CH$_3$C$_6$H$_5$) P(C$_6$H$_5$)$_2$)ZrCl] was obtained with the isolated yield of 85%. Following are the compound's data of NMR and element analysis: $^1$H NMR (300 MHz, CDCl$_3$, Me$_4$Si) d 2.18 (s, 3H), 2.34 (s, 3H), 5.89 (s, 10H), 6.73-6.79 (m, 4H), 6.92-6.95 (m, 2H), 7.09-7.11 (m, 2H), 7.40-7.42 (m, 6H), 7.76-7.78 (m, 4H); $^{13}$C NMR (75 MHz, CDCl$_3$, Me$_4$Si) d 21.2, 111.1, 124.9, 128.5, 128.6 (d, $^3J_{PC}$=7.9 Hz), 129.0 (d, $^3J_{PC}$=2.9 Hz), 129.2, 129.60 (d, $^4J_{PC}$=1.4 Hz), 132.7 (d, $^2J_{PC}$=10.0 Hz), 133.2 (d, $^1J_{PC}$=17.9 Hz), 134.2, 135.1 (d, $^2J_{PC}$=2.9 Hz), 135.8, 137.3 (d, $^1J_{PC}$=40.2 Hz), 147.6 (d, $^3J_{PC}$=40.2 Hz), 214.5 (d, $^2J_{PC}$=20.1 Hz); $^{31}$P NMR (81 MHz, CDCl$_3$, 85% H$_3$PO$_4$) d - 41.0; Positive ion ESI-MS: 611.0 (M$^+$); element analysis (C$_{38}$H$_{34}$ClPZr) theoretical values (%): C 70.40, H 5.29, Cl, 5.47, P 4.78; experimental values (%): C 70.77, H 5.44, Cl 5.28, P 4.55.

EXAMPLE 8

Preparation for Dicylopentadienyl (1,2-diethyl-vinyl dimethylphosphine) zirconium chloride [8: Cp$_2$(C(C$_2$H$_5$)=C(C$_2$H$_5$)P(CH$_3$)$_2$)ZrCl]

The experimental procedures were the same as those of Example 1, except that the alkyne was substituted with 3-hexyne (1.0 mmol) with the simultaneous use of ClPMe$_2$ (1.0 mmol). After separation, 200 mg white solid 2-cyclopentadienyl zirconium chloride-1,2-diethyl-vinyl dimethylphosphine was obtained with the isolated yield of 74%. The compound's theoretical values (%) and experimental values (%) of the element analysis (C$_{18}$H$_{26}$ClPZr) were respectively C 54.04, H 6.55, Cl 8.86, P 7.74 and C 54.45, H 6.21; Cl 8.59; P 7.59.

EXAMPLE 9

Preparation for Dicylopentadienyl (1-phenyl-2-ethyl-vinyl dimethylphosphine) zirconium chloride [9: Cp$_2$(C(C$_2$H$_5$)=C(C$_6$H$_5$)P(CH$_3$)$_2$)ZrCl]

The experimental procedures were the same as those of Example 1, except that the alkyne was substituted with 1-phenyl-1-hutyne (1.0 mmol) with the simultaneous use of ClPMe$_2$ (1.0 mmol). After separation, 170 mg white solid cyclopentadienyl (1-phenyl-2-ethyl-vinyl dimethylphosphine) zirconium chloride (9) was obtained with the isolated yield of 38%. The compound's theoretical values (%) and experimental values (%) of the element analysis (C$_{22}$H$_{26}$ClPZr) were respectively C, 58.97; H, 5.85, Cl 7.91, P 6.91 and C 59.26, H 6.21; Cl 7.76; P 6.83.

EXAMPLE 10

Preparation for Dicylopentadienyl (1-ethyl-2-phenyl-vinyl dimethylphosphine) zirconium chloride [10: $Cp_2(C(C_6H_5)=C(C_2H_5)P(CH_3)_2)ZrCl]$ The experimental procedures were the same as those of Example 1, except that the alkyne was substituted with 1-phenyl-1-hutyne (1.0 mmol) with the simultaneous use of $ClPMe_2$ (1.0 mmol). After separation, 85 mg white solid cyclopentadienyl zirconium chloride (1-ethyl-2-phenyl-vinyl dimethylphosphine) was obtained with the isolated yield of 19%. The compound's theoretical values (%) and experimental values (%) of the element analysis ($C_{22}H_{26}ClPZr$) were respectively C 58.97, H 5.85, Cl, 7.91, P 6.91 and C 59.13, H 6.26; Cl 7.88; P 6.76.

EXAMPLE 11

Preparation for Dicylopentadienyl (1,2-dipropyl-vinyl dimethylphosphine) zirconium chloride [11: $Cp_2(C(C_3H_7)=C(C_3H_7)P(CH_3)_2)ZrCl]$ The experimental procedures were the same as those of Example 1, except that the alkyne was substituted with 4-octyne (11.0 mmol) with the simultaneous use of $ClPMe_2$ (1.0 mmol). After separation, 278 mg white solid 2-cyclopentadienyl (1,2-dipropyl-vinyl dimethylphosphine) zirconium chloride (11) was obtained with the isolated yield of 65%. The compound's theoretical values (%) and experimental values (%) of the element analysis ($C_{20}H_{30}ClPZr$) were respectively C 56.11, H 7.06, Cl 8.28, P 7.24 and C 54.23, H 7.44; Cl 7.95; P 6.96.

EXAMPLE 12

Preparation for Dicylopentadienyl (1,2-dibutyl-vinyl dimethylphosphine) zirconium chloride [12: $Cp_2(C(C_4H_9)=C(C_4H_9)P(CH_3)_2)ZrCl]$ The experimental procedures were the same as those of Example 1, except that the alkyne was substituted with 5-decyne (11.0 mmol) with the simultaneous use of $ClPMe_2$ (1.0 mmol). After separation, 319 mg white solid 2-cyclopentadienyl (1,2-dibutyl-vinyl dimethylphosphine) zirconium chloride (12) was obtained with the isolated yield of 70%. The compound's theoretical values (%) and experimental values (%) of the element analysis ($C_{22}H_{34}ClPZr$) were respectively C 57.93, H 7.51, Cl 7.77, P 6.79 and C 58.19, H 7.80; Cl 7.88; P 6.76.

EXAMPLE 13

Preparation for Dicylopentadienyl (1,2-diphenyl-vinyl dimethylphosphine) zirconium chloride [13: $Cp_2(C(C_6H_5)=C(C_6H_5)P(CH_3)_2)ZrCl]$ The experimental procedures were the same as those of Example 1, except that the alkyne was substituted with diphenyl acetylene (1.0 mmol) with the simultaneous use of $ClPMe_2$ (1.0 mmol). After separation, 407 mg white solid 2-cyclopentadienyl (1,2-diphenyl-vinyl dimethylphosphine) zirconium chloride (13) was obtained with the isolated yield of 82%. The compound's theoretical values (%) and experimental values (%) of the element analysis ($C_{26}H_{26}ClPZr$) were respectively C 62.94, H 5.28, Cl 7.15, P 6.24 and C 63.15, H 5.57; Cl 6.94; P 6.11.

EXAMPLE 14

Preparation for Dicylopentadienyl (1,2-di(4-methylphenyl)-vinyl dimethylphosphine) zirconium chloride [14: $Cp_2(C(CH_3C_6H_5)=C(CH_3C_6H_5)P(CH_3)_2)ZrCl]$ The experimental procedures were the same as those of Example 1, except that the alkyne was substituted with di(4-methylphenyl)-acetylene (11.0 mmol) with the simultaneous use of $ClPMe_2$ (1.0 mmol). After separation, 550 mg white solid 2-cyclopentadienyl (1,2-di(4-methylphenyl)-vinyl dimethylphosphine zirconium chloride (14) was obtained with the isolated yield of 77%. The compound's theoretical values (%) and experimental values (%) of the element analysis ($C_{28}H_{30}ClPZr$) were respectively C 64.16, H 5.77, Cl 6.76, P 5.91 and C 64.47, H 6.11; Cl 6.54; P 6.01.

EXAMPLE 15

Preparation for Dicylopentadienyl zirconium chloride-1,2-diethyl-vinyl diisopropylphosphine [15: $Cp_2(C(C_2H_5)=C(C_2H_5)P(i-C_3H_7)_2)ZrCl]$ The experimental procedures were the same as those of Example 1, except that the alkyne was substituted with 3-hexyne (1.0 mmol) with the simultaneous use of $ClP(i-Pr)_2$ (1.0 mmol). After separation, 287 mg white solid 2-cyclopentadienyl zirconium chloride-1,2-diethyl-vinyl diisopropylphosphine (15) was obtained with the isolated yield of 63%. The compound's theoretical values (%) and experimental values (%) of the element analysis ($C_{22}H_{34}ClPZr$) were respectively C 57.93, H 7.51, Cl 7.77, P 6.79 and C 60.21, H 7.73; Cl 7.54; P 6.48.

EXAMPLE 16

Preparation for Dicylopentadienyl (1-phenyl-2-ethyl-vinyl diisopropylphosphine) zirconium chloride [16: $Cp_2(C(C_6H_5)=C(C_2H_5)P(i-C_3H_7)_2)ZrCl]$ The experimental procedures were the same as those of Example 1, except that the alkyne was substituted with 1-phenyl-1-butyne (11.0 mmol) with the simultaneous use of $ClP(i-Pr)_2$ (1.0 mmol). After separation, 176 mg white solid 2-cyclopentadienyl (1-phenyl-2-ethyl-vinyl diisopropylphosphine) zirconium chloride (16) was obtained with the isolated yield of 35%. The compound's theoretical values (%) and experimental values (%) of the element analysis ($C_{26}H_{34}ClPZr$) were respectively C 61.84, H 6.80, Cl 7.03, P 6.14 and C 62.11, H 7.09; Cl 6.87; P 5.93.

EXAMPLE 17

Preparation for Dicylopentadienyl (1-ethyl-2-phenyl-vinyl diisopropylphosphine) zirconium chloride [17: $Cp_2(C(C_2H_5)=C(C_6H_5)P(i-C_3H_7)_2)ZrCl]$ The experimental procedures were the same as those of Example 1, except that the alkyne was substituted with 1-phenyl-1-butyne (1.0 mmol) with the simultaneous use of $ClP(i-Pr)_2$ (1.0 mmol). After separation, 76 mg white solid 2-cyclopentadienyl (1-ethyl-2-phenyl-vinyl diisopropylphosphine) zirconium chloride (17) was obtained with the isolated yield of 15%. The compound's theoretical values (%) and experimental values (%) of the element analysis ($C_{26}H_{34}ClPZr$)

were respectively C 61.84, H 6.80, Cl, 7.03, P 6.14 and C 62.07, H 6.96; Cl 7.33; P 6.01.

EXAMPLE 18

Preparation for Dicylopentadienyl (1,2-dipropyl-vinyl diisopropylphosphine) zirconium chloride [18: $Cp_2(C(C_3H_7)=C(C_3H_7)P(i-C_3H_7)_2)ZrCl$]

The experimental procedures were the same as those of Example 1, except that the alkyne was substituted with 4-octyne (1.0 mmol) with the simultaneous use of ClP(i-Pr)$_2$ (1.0 mmol). After separation, 305 mg white solid 2-cyclopentadienyl (1,2-dipropyl-vinyl diisopropylphosphine) zirconium chloride (18) was obtained with the isolated yield of 63%. The compound's theoretical values (%) and experimental values (%) of the element analysis ($C_{24}H_{38}ClPZr$) were respectively C 59.53, H 7.91, Cl 7.32, P 6.40 and C 59.37, H 8.03; Cl 7.45; P 6.23.

EXAMPLE 19

Preparation for Dicylopentadienyl (1,2-dibutyl-vinyl diisopropylphosphine) zirconium chloride [19: $Cp_2(C(C_4H_9)=C(C_4H_9)P(i-C_3H_7)_2)ZrCl$]

The experimental procedures were the same as those of Example 1, except that the alkyne was substituted with 5-decyne (11.0 mmol) with the simultaneous use of ClP(i-Pr)$_2$ (1.0 mmol). After separation, 440 mg white solid 2-cyclopentadienyl (1,2-dibutyl-vinyl diisopropylphosphine) zirconium chloride (19) was obtained with the isolated yield of 86%. Following are the compound's data of NMR and element analysis: $^1$H NMR (300 MHz, CDCl$_3$, Me$_4$Si) d 0.93 (t, J=6.8 Hz, 3H), 0.96 (t, J=7.2 Hz, 3H), 1.14-1.50 (m, 20H), 2.01-2.10 (m, 2H), 2.14-2.33 (m, 4H), 6.00 (s, 10H); $^{13}$C NMR (75 MHz, CDCl$_3$, Me$_4$Si) d 14.0, 14.2, 20.4, 20.8 (d, $^2J_{PC}$=5.7 Hz), 23.6, 24.2, 25.9 (d, $^1J_{PC}$=2.2 Hz), 31.5, 32.0 (d, $^4J_{PC}$=3.6 Hz), 32.4 (d, $^3J_{PC}$=5.0 Hz), 38.9 (d, $^3$PC=33.0 Hz), 109.6 (10C), 140.5 (d, $^1J_{PC}$=34.4 Hz), 209.4 (d, $^2J_{PC}$=14.1 Hz); $^{31}$P NMR (81 MHz, CDCl$_3$, 85% H$_3$PO$_4$) d -30.9; Positive ion ESI-MS: 475.0 (M$^+$); element analysis ($C_{26}H_{42}ClPZr$) theoretical values (%): C 60.96, H 8.26, Cl, 6.92, P 6.05; experimental values (%): C 60.87, H 8.35, Cl 6.77, P 6.01.

EXAMPLE 20

Preparation for Dicylopentadienyl (1,2-diphenyl-vinyl diisopropylphosphine) zirconium chloride [20: $Cp_2(C(C_6H_5)=C(C_6H_5)P(i-C_3H_7)_2)ZrCl$]

The experimental procedures were the same as those of Example 1, except that the alkyne was substituted with diphenyl acetylene (1.0 mmol) with the simultaneous use of ClP (i-Pr)$_2$ (1.0 mmol). After separation, 460 mg white solid 2-cyclopentadienyl (1,2-diphenyl-vinyl diisopropylphosphine) zirconium chloride (20) was obtained with the isolated yield of 84%. Following are the compound's data of NMR and element analysis: $^1$H NMR (300 MHz, CDCl$_3$, Me$_4$Si) d 1.25 (dd, J=7.2 Hz, $^3J_{PH}$=12.4 Hz, 6H), 1.48 (dd, J=7.2 Hz, $^3J_{PH}$=14.8 Hz, 6H), 2.51 (m, J=7.2 Hz, $^2J_{PH}$=3.1 Hz, 2H), 6.08 (s, 10H), 6.85-7.13 (m, 10H); $^{13}$C NMR (75 MHz, CDCl$_3$, Me$_4$Si) d 19.9, 20.8 (d, $^2J_{PC}$=5.7 Hz), 26.7 (d, $^1J_{PC}$=2.9 Hz), 110.5, 124.2, 125.2, 125.9, 127.9, 128.3, 140.8 (d, $^2J_{PC}$=2.2 Hz), 140.9 (d, $^1J_{PC}$=33.0 Hz), 150.6 (d, $^3J_{PC}$=34.4 Hz, 1C), 209.6 (d, $^2J_{PC}$=23.7 Hz); $^{31}$P NMR (81 MHz, CDCl$_3$, 85% H$_3$PO$_4$) d-24.6; Positive ion ESI-MS: 515.1 (M$^+$); element analysis ($C_{30}H_{34}ClPZr$) theoretical values (%): C 65.25, H 6.21, Cl 6.42, P 5.61; experimental values (%): C 65.03, H 6.38, Cl 6.17, P 5.48.

EXAMPLE 21

Preparation for Dicylopentadienyl (1,2-di(4-methylphenyl)-vinyl diisopropylphosphine) zirconium chloride [21: $Cp_2(C(4-CH_3C_6H_5)=C(4-CH_3C_6H_5)P(i-C_3H_7)_2)ZrCl$]

The experimental procedures were the same as those of Example 1, except that the alkyne was substituted with di(4-methylphenyl)-acetylene (11.0 mmol) with the simultaneous use of ClP (i-Pr)$_2$ (1.0 mmol). After separation, 499 mg white solid 2-cyclopentadienyl (1,2-di(4-methylphenyl)-vinyl diisopropylphosphine) zirconium chloride (21) was obtained with the isolated yield of 86%. The compound's theoretical values (%) and experimental values (%) of the element analysis ($C_{30}H_{34}ClPZr$) were respectively C 66.23, H 6.60, Cl 6.11, P 5.34 and C 65.99, H 6.45; Cl 6.42; P 5.18.

EXAMPLE 22

Preparation for Dicylopentadienyl (1,2-diethyl-vinyl dicyclohexylphosphine) zirconium chloride [22: $Cp_2(C(C_2H_5)=C(C_2H_5)P(C_6H_{11})_2)ZrCl$]

The experimental procedures were the same as those of Example 1, except that the alkyne was substituted with 3-hexyne (1.0 mmol) with the simultaneous use of ClP Cy$_2$ (1.0 mmol). After separation, 322 mg white solid 2-cyclopentadienyl (1,2-diethyl-vinyl dicyclohexylphosphine) zirconium chloride (22) was obtained with the isolated yield of 60%. The compound's theoretical values (%) and experimental values (%) of the element analysis ($C_{28}H_{30}ClPZr$) were respectively C 62.71, H 7.89, Cl 6.61, P 5.78 and C 62.98, H 8.01; Cl 6.51; P, 5.67.

EXAMPLE 23

Preparation for Dicylopentadienyl (1-phenyl-2-ethyl-vinyl dicyclohexylphosphine) zirconium chloride [23: $Cp_2(C(C_6H_5)=C(C_2H_5)P(C_6H_{11})_2)ZrCl$]

The experimental procedures were the same as those of Example 1, except that the alkyne was substituted with 1-phenyl-1-butyne (1.0 mmol) with the simultaneous use of ClP Cy$_2$ (1.0 mmol). After separation, 175 mg white solid 2-cyclopentadienyl (1-phenyl-2-ethyl-vinyl dicyclohexylphosphine) zirconium chloride (23) was obtained with the isolated yield of 30%. The compound's theoretical values (%) and experimental values (%) of the element analysis ($C_{32}H_{42}ClPZr$) were respectively C 65.78, H 7.24, Cl, 6.07, P 5.30 and C 65.66, H 7.55; Cl 5.83; P 5.11.

EXAMPLE 24

Preparation for Dicylopentadienyl (1-ethyl-2-phenyl-vinyl dicyclohexylphosphine) zirconium chloride [24: $Cp_2(C(C_2H_5)=C(C_6H_5)P(C_6H_{11})_2)ZrCl$]

The experimental procedures were the same as those of Example 1, except that the alkyne was substituted with 1-phenyl-1-butyne (11.0 mmol) with the simultaneous use of ClP Cy$_2$ (1.0 mmol). After separation, 99 mg white solid 2-cyclopentadienyl (1-ethyl-2-phenyl-vinyl dicyclohexylphosphine)

zirconium chloride (24) was obtained with the isolated yield of 17%. The compound's theoretical values (%) and experimental values (%) of the element analysis ($C_{32}H_{12}ClPZr$) were respectively C 65.78, H 7.24, Cl 6.07, P 5.30 and C 66.06, H 7.53; Cl 5.98; P 5.12.

EXAMPLE 25

Preparation for Dicylopentadienyl (1,2-dipropyl-vinyl dicyclohexylphosphine) zirconium chloride [25: $Cp_2(C(C_3H_7)=C(C_3H_7)P(C_6H_{11})_2)ZrCl$]

The experimental procedures were the same as those of Example 1, except that the alkyne was substituted with 4-octyne (1.0 mmol) with the simultaneous use of ClP $Cy_2$ (1.0 mmol). After separation, 372 mg white solid 2-cyclopentadienyl (1,2-dipropyl-vinyl dicyclohexylphosphine) zirconium chloride (25) was obtained with the isolated yield of 66%. The compound's theoretical values (%) and experimental values (%) of the element analysis ($C_{30}H_{34}ClPZr$) were respectively C 63.85, H 8.22, Cl 6.28, P 5.49 and C 64.04, H 8.53; Cl 6.07; P 5.58.

EXAMPLE 26

Preparation for Dicylopentadienyl (1,2-dibutyl-vinyl dicyclohexylphosphine) zirconium chloride [26: $Cp_2(C(C_4H_9)=C(C_4H_9)P(C_6H_{11})_2)ZrCl$]

The experimental procedures were the same as those of Example 1, except that the alkyne was substituted with 5-decyne (11.0 mmol) with the simultaneous use of ClP $Cy_2$ (1.0 mmol). After separation, 414 mg white solid 2-cyclopentadienyl (1,2-dibutyl-vinyl dicyclohexylphosphine) zirconium chloride (26) was obtained with the isolated yield of 70%. The compound's theoretical values (%) and experimental values (%) of the element analysis ($C_{32}H_{50}ClPZr$) were respectively C 63.85, H 8.22, Cl 6.28, P 5.49 and C 64.01, H 8.58; Cl 6.17; P 5.09.

EXAMPLE 27

Preparation for Dicylopentadienyl (1,2-diphenyl-vinyl dicyclohexylphosphine) zirconium chloride [27: $Cp_2(C(C_6H_5)=C(C_6H_5)P(C_6H_{11})_2)ZrCl$]

The experimental procedures were the same as those of Example 1, except that the alkyne was substituted with diphenyl acetylene (1.0 mmol) with the simultaneous use of ClP $Cy_2$ (1.0 mmol). After separation, 537 mg white solid 2-cyclopentadienyl (1,2-diphenyl-vinyl dicyclohexylphosphine) zirconium chloride (27) was obtained with the isolated yield of 85%. The compound's theoretical values (%) and experimental values (%) of the element analysis ($C_{36}H_{42}ClPZr$) were respectively C 68.38, H 6.69, Cl 15.61, P 4.90 and C 68.65, H 6.87; Cl 5.32; P 5.01.

EXAMPLE 28

Preparation for Dicylopentadienyl (1,2-di(4-methylphenyl)-vinyl dicyclohexylphosphine) zirconium chloride [28: $Cp_2(C(4-CH_3C_6H_5)=C(4-CH_3C_6H_5)P(C_6H_{11})_2)ZrCl$]

The experimental procedures were the same as those of Example 1, except that the alkyne was substituted with di(4-methylphenyl)-acetylene (1.0 mmol) with the simultaneous use of ClP $Cy_2$ (1.0 mmol). After separation, 548 mg white solid 2-cyclopentadienyl (1,2-di(4-methylphenyl)-vinyl dicyclohexylphosphine) zirconium chloride (28) was obtained with the isolated yield of 83%. The compound's theoretical values (%) and experimental values (%) of the element analysis ($C_{38}H_{46}ClPZr$) were respectively C 69.11, H 7.02, Cl 5.37, P 4.69 and C 79.47, H 7.26; Cl 5.19; P 4.57.

EXAMPLE 29

Preparation for Dicylopentadienyl (1,2-diphenyl-vinyl diphenylphosphine) titanium chloride [29: $Cp_2(C(C_6H_5)=C(C_6H_5)P(C_6H_5)_2)TiCl$]

(1) Under the protection of highly pure nitrogen gas, 1.2 mmol titanocene dichloride and 5 ml tetrahydrofuran solvent treated by freedom of oxygen and water were added into a 20 ml Schlenk reaction tube and stirred uniformly to form a first mixture; the first mixture was cooled to −78° C. with dry ice-acetone bath or liquid nitrogen-acetone bath; and then 2.4 mmol n-butyl lithium solution was added and kept for 30 min to form a second mixture.

(2) N,N-dimethyl-4-methylaminopyridine (DMAP) (2.0 mmol) was added into the second mixture and reacted at room temperature for 1 hour to form a third mixture; diphenylacetylene (1.0 mmol) was added into the third mixture and stirred continuously for 1 hour; and then $ClPPh_2$(1.0 mmol) was add and stirred for 1 hour at this temperature to form a fourth mixture.

(3) 2 mL dilute hydrochloric acid (3M) was added into the fourth mixture to form a product; the product was extracted with 30 ml dichloromethane three times to form the filtrates; the filtrates were combined and concentrated by rotary evaporation to obtain the coarse products.

(4) The coarse products were column-separated (300 mesh silica gel) with petroleum ether/tetrahydrofuran (10/1) as the eluant to obtain 490 mg white solid 2-cylopentadienyl zirconium chloridate-1,2-diphenyl-vinyl diphenylphosphine with the isolated yield of 85%. The theoretical values (%) and experimental values (%) of the element analysis ($C_{36}H_{30}ClPTi$) were respectively C 75.95, H 5.24, Cl 6.15, P 5.37 and C 75.90; H 5.16, Cl 6.02, P 5.13.

EXAMPLE 30

Preparation for Dicylopentadienyl (1,2-dibutyl-vinyl diphenylphosphine) titanium chloride [30: $Cp_2(C(C_4H_9)=C(C_4H_9)P(C_6H_5)_2)TiCl$]

The experimental procedures were the same as those of Example 29, except that the alkyne was substituted with 5-decyne (1.0 mmol). After separation, 3768 mg white solid 2-cyclopentadienyl titanium chloride (1,2-dibutyl-vinyl dicyclohexylphosphine) was obtained with the isolated yield of 70%. The compound's theoretical values (%) and experimental values (%) of the element analysis ($C_{32}H_{38}ClPZr$) were respectively C 71.58, H 7.13, Cl 6.60, P 5.77 and C 71.42, H 7.18; Cl 6.48; P 5.82.

EXAMPLE 31

Preparation for Dicylopentadienyl (1,2-diphenyl-vinyl diphenylphosphine) hafnium chloride [31: $Cp_2(C(C_6H_5)=C(C_6H_5)P(C_6H_5)_2)HfCl$]

(1) Under the protection of highly pure nitrogen gas, 1.2 mmol hafnocene dichloride and 5 ml tetrahydrofuran solvent treated by freedom of oxygen and water were added into a 20 ml Schlenk reaction tube and stirred uniformly to form a first mixture; the first mixture was cooled to −78° C. with dry ice-acetone bath or liquid nitrogen-acetone bath; and then 2.4 mmol n-butyl lithium solution was added and kept for 30 min to form a second mixture.

(2) N,N-dimethyl-4-methylaminopyridine (DMAP) (2.0 mmol) was added into the second mixture and reacted at room temperature for 1 hour to form a third mixture; diphenylacetylene (1.0 mmol) was added into the third mixture and stirred continuously for 1 hour; and then ClPPh$_2$(1.0 mmol) was add and stirred for 1 hour at this temperature to form a fourth mixture.

(3) 2 mL dilute hydrochloric acid (3M) was added into the fourth mixture to form a product; the product was extracted with 30 ml dichloromethane three times to form the filtrates; the filtrates were combined and concentrated by rotary evaporation to obtain the coarse products.

(4) The coarse products were column-separated (300 mesh silica gel) with petroleum ether/tetrahydrofuran (10/1) as the eluant to obtain 490 mg white solid 2-cylopentadienyl hafnium chloride-1,2-diphenyl-vinyl diphenylphosphine with the isolated yield of 88%. The theoretical values (%) and experimental values (%) of the element analysis (C$_{36}$H$_{30}$ClPHf) were respectively C 61.11, H 4.27, Cl 5.01, P 4.38 and C 60.88, H 4.216, Cl 4.96, P 4.52.

EXAMPLE 32

The Polymerization of Ethylene Catalyzed by Complex 1

80 ml toluene, 10.3 ml methyl aluminoxane (MAO) (1.46 mol/l in toluene) and 20 ml catalyst 1 (1 μmol) in toluene solution were added into a 500-ml stainless steel autoclave, and mechanical stirring was begun and kept at 200 rpm. When the polymerization temperature reached 25° C., ethylene was filled into the autoclave and polymerization began. The ethylene pressure was kept at 3 MPa, and stirring reaction lasted 30 min to obtain a polymer. The resulting polymer was washed with ethanol solution acidified by 5% hydrochloric acid and dried in a drying vacuum oven at 60° C. to constant weight. 53.1 g polymer was obtained, and the polymerization activity was 1.06×10$^8$ g·mol$^{-1}$·h$^{-1}$. The weight-average molecular weight and number-average molecular weight of the obtained polymer was respectively Mw=1.91×10$^5$ g·mol$^{-1}$ and Mn=3.72×10$^4$ g·mol$^{-1}$, and PDI=5.13.

EXAMPLE 33-62

The Polymerization of Ethylene Catalyzed by Complex 2-31

The operation process and reaction conditions of the polymerizations were the same as those of Example 32. The used catalysts were respectively compounds 2-31. The results of the polymerizations are shown in Table 1.

EXAMPLE 63-64

The Polymerization of Ethylene Catalyzed by Metallocene Catalysts

The operation process and reaction conditions of the polymerizations were the same as those of Example 32. The used catalysts were respectively Cp$_2$ZrCl$_2$ and Cp$_2$TiCl$_2$. The results of the polymerizations are shown in Table 1.

TABLE 1

Results of catalyzed ethylene polymerization

| Example | Catalyst | PE/g | polymerization activity/ gmol$^{-1}$·h$^{-1}$ | Mw × 10$^{-5}$ | Mn × 10$^{-4}$ | PDI |
|---|---|---|---|---|---|---|
| 33 | 2 | 78.5 | 1.57 × 10$^8$ | 1.81 | 3.87 | 4.68 |
| 34 | 3 | 53.1 | 1.06 × 10$^8$ | 2.48 | 4.06 | 6.11 |
| 35 | 4 | 62.7 | 1.25 × 10$^8$ | 3.08 | 6.85 | 4.50 |
| 36 | 5 | 78.1 | 1.56 × 10$^8$ | 1.61 | 3.62 | 4.45 |
| 37 | 6 | 72.8 | 1.46 × 10$^8$ | 1.47 | 2.88 | 5.11 |
| 38 | 7 | 78.8 | 1.58 × 10$^8$ | 1.36 | 3.62 | 3.76 |
| 39 | 8 | 75.6 | 1.51 × 10$^8$ | 1.59 | 2.97 | 5.35 |
| 40 | 9 | 55.8 | 1.12 × 10$^8$ | 2.06 | 3.69 | 5.58 |
| 41 | 10 | 66.3 | 1.33 × 10$^8$ | 2.49 | 4.16 | 5.99 |
| 42 | 11 | 47.6 | 9.52 × 10$^7$ | 2.16 | 4.05 | 5.33 |
| 43 | 12 | 50.5 | 1.01 × 10$^8$ | 1.49 | 3.06 | 4.87 |
| 44 | 13 | 53.5 | 1.07 × 10$^8$ | 1.69 | 3.57 | 4.73 |
| 45 | 14 | 59.8 | 1.20 × 10$^8$ | 1.85 | 3.84 | 4.82 |
| 46 | 15 | 77.1 | 1.54 × 10$^8$ | 2.06 | 4.06 | 5.07 |
| 47 | 16 | 79.6 | 1.59 × 10$^8$ | 2.46 | 4.59 | 5.36 |
| 48 | 17 | 72.7 | 1.45 × 10$^8$ | 1.92 | 5.02 | 3.82 |
| 49 | 18 | 69.9 | 1.40 × 10$^8$ | 2.69 | 5.41 | 4.97 |
| 50 | 19 | 63.2 | 1.26 × 10$^8$ | 3.07 | 6.31 | 4.87 |
| 51 | 20 | 87.1 | 1.74 × 10$^8$ | 1.41 | 2.47 | 5.72 |
| 52 | 21 | 48.7 | 9.74 × 10$^7$ | 2.36 | 4.52 | 5.22 |
| 53 | 22 | 47.5 | 9.50 × 10$^7$ | 3.45 | 6.73 | 5.13 |
| 54 | 23 | 40.8 | 8.16 × 10$^7$ | 2.68 | 5.62 | 4.77 |
| 55 | 24 | 45.9 | 9.18 × 10$^7$ | 2.64 | 6.04 | 4.37 |
| 56 | 25 | 55.1 | 1.10 × 10$^8$ | 1.97 | 4.29 | 4.59 |
| 57 | 26 | 58.7 | 1.17 × 10$^8$ | 2.15 | 5.16 | 4.17 |
| 58 | 27 | 60.8 | 1.22 × 10$^8$ | 1.83 | 4.91 | 3.73 |
| 59 | 28 | 68.7 | 1.37 × 10$^8$ | 2.06 | 6.20 | 3.32 |
| 60 | 29 | 39.9 | 7.98 × 10$^7$ | 3.95 | 7.08 | 5.58 |
| 61 | 30 | 36.2 | 7.24 × 10$^7$ | 4.08 | 7.27 | 5.61 |
| 62 | 31 | 30.2 | 6.04 × 10$^7$ | 5.36 | 9.43 | 5.68 |
| 63 | Cp$_2$ZrCl$_2$ | 21.9 | 4.39 × 10$^7$ | 1.89 | 9.36 | 2.02 |
| 64 | Cp$_2$TiCl$_2$ | 15.9 | 3.18 × 10$^7$ | 3.79 | 13.88 | 2.13 |

EXAMPLE 65

The Polymerization of Ethylene Catalyzed by Complex 5

The operation process and the catalyst of the polymerizations were the same as those of Example 36. Except that the ethylene pressure was 1 MPa, the other reaction conditions were the same as those of Example 36. 30.6 g polymer was obtained, and the polymerization activity was 6.12×10$^7$ g·mol$^{-1}$·h$^{-1}$. The weight-average molecular weight and number-average molecular weight of the obtained polymer were respectively Mw=1.94×10$^5$ g·mol$^{-1}$ and Mn=3.05×10$^4$ g·mol$^{-1}$, and PDI=6.36.

EXAMPLE 66

The Polymerization of Ethylene Catalyzed by Complex 5

The operation process and the catalyst of the polymerizations were the same as those of Example 36. Except that the ethylene pressure was 2 MPa, the other reaction conditions were the same as those of Example 36. 52.3 g polymer was obtained, and the polymerization activity was 1.04× 10$^8$ g·mol$^{-1}$·h$^{-1}$. The weight-average molecular weight and number-average molecular weight of the obtained polymer was respectively Mw=$2.13\times10^5$ g·mol$^{-1}$ and Mn=$3.16\times10^4$ g·mol$^{-1}$, and PDI=6.74.

EXAMPLE 67

The Polymerization of Ethylene Catalyzed by Complex 5

The operation process and the catalyst of the polymerizations were the same as those of Example 36. Except that 5.1 ml methyl aluminoxane (MAO) (1.46 mol/l in toluene) and 5 μmol catalyst 1 were employed. The reaction lasted 5 min. The other reaction conditions were the same as those of Example 36. 42.0 g polymer was obtained, and the polymerization activity was $1.01\times10^8$ g·mol$^{-1}$·h$^{-1}$. The weight-average molecular weight and number-average molecular weight of the obtained polymer was respectively Mw=$1.72\times10^5$ g·mol$^{-1}$ and Mn=$2.83\times10^4$ g·mol$^{-1}$, and PDI=6.07.

EXAMPLE 68

The Polymerization of Ethylene Catalyzed by Complex 5

The operation process and the catalyst of the polymerizations were the same as those of Example 36. Except that 5.1 ml methyl aluminoxane (MAO) (1.46 mol/l in toluene) and 0.5 μmol catalyst were employed, the other reaction conditions were the same as those of Example 36. 59.2 g polymer was obtained, and the polymerization activity was $2.37\times10^8$ g~mol$^{-1}$·h$^{-1}$. The weight-average molecular weight and number-average molecular weight of the obtained polymer was respectively Mw=$1.61\times10^5$ g·mol$^{-1}$ and Mn=$3.62\times10^4$ g·mol$^{-1}$, and PDI=4.45.

EXAMPLE 69

The Polymerization of Ethylene Catalyzed by Complex 5

The operation process and the catalyst of the polymerizations were the same as those of Example 36. Except that 3.9 ml modified methyl aluminoxane (MMAO) (1.90 mol/l in hexane) and 5 μmol catalyst were employed. The reaction lasted 15 min. The other reaction conditions were the same as those of Example 36. 57.4 g polymer was obtained, and the polymerization activity was $4.59\times10^7$ g·mol$^{-1}$·h$^{-1}$. The weight-average molecular weight and number-average molecular weight of the obtained polymer was respectively Mw=$1.03\times10^5$ g·mol$^{-1}$ and Mn=$1.83\times10^4$ g·mol$^{-1}$, and PDI=5.64.

EXAMPLE 70

The Polymerization of Ethylene Catalyzed by Complex 5

The operation process and the catalyst of the polymerizations were the same as those of Example 36. Except that 7.9 ml methyl aluminoxane (MAO) (1.46 mol/l in hexane) was employed, the other reaction conditions were the same as those of Example 36. 58.7 g polymer was obtained, and the polymerization activity was $1.17\times10^8$ g·mol$^{-1}$·h$^{-1}$. The weight-average molecular weight and number-average molecular weight of the obtained polymer was respectively Mw=$0.88\times10^5$ g·mol$^{-1}$ and Mn=$1.94\times10^4$ g·mol$^{-1}$, and PDI=4.56.

EXAMPLE 71

The Polymerization of Ethylene Catalyzed by Complex 5

The operation process and the catalyst of the polymerizations were the same as those of Example 36. Except that 3.9 ml modified methyl aluminoxane (MMAO) (1.90 mol/l in hexane) and 0.51 mmol catalyst were employed, the other reaction conditions were the same as those of Example 36. 22.9 g polymer was obtained, and the polymerization activity was $9.16\times10^7$ g·mol$^{-1}$·h$^{-1}$. The weight-average molecular weight and number-average molecular weight of the obtained polymer was respectively Mw=$1.03\times10^5$ g·mol$^{-1}$ and Mn=$2.16\times10^4$ g·mol$^{-1}$, and PDI=4.77.

EXAMPLE 72-86

The Polymerization of Ethylene Catalyzed by Complex 6

The operation process and the catalysts were the same as those in Example 37. The polymerization conditions and results are shown in the following table:

| Example | Catalyst (μmol) | Cocatalyst | Al/Zr | Reaction time (min) | Temperature (°C.) | Activity/ gmol$^{-1}$·h$^{-1}$ | $M \times 10^{-5}$ | $M \times 10^{-4}$ | PDI |
|---|---|---|---|---|---|---|---|---|---|
| 72 | 5 | MAO | 1500 | 5 | 25 | $4.42 \times 10^7$ | 2.82 | 6.20 | 4.55 |
| 73 | 2.5 | MAO | 3000 | 30 | 25 | $1.46 \times 10^6$ | 3.06 | 6.42 | 4.77 |
| 74 | 2.5 | MAO | 5000 | 30 | 25 | $2.42 \times 10^7$ | 2.75 | 5.93 | 4.64 |
| 75 | 2.5 | MAO | 10000 | 30 | 25 | $5.87 \times 10^7$ | 2.91 | 6.17 | 4.72 |
| 76 | 2 | MAO | 5000 | 30 | 25 | $1.34 \times 10^6$ | 2.81 | 6.04 | 4.65 |
| 77 | 2 | MAO | 10000 | 30 | 25 | $2.31 \times 10^7$ | 2.83 | 5.99 | 4.72 |
| 78 | 2 | MAO | 15000 | 30 | 25 | $6.60 \times 10^7$ | 3.04 | 6.35 | 4.80 |
| 79 | 1 | MAO | 10000 | 30 | 25 | $4.42 \times 10^7$ | 3.39 | 5.45 | 6.22 |
| 80 | 1 | MAO | 20000 | 30 | 25 | $3.34 \times 10^7$ | 0.54 | 1.81 | 2.95 |
| 81 | 0.5 | MAO | 15000 | 30 | 25 | $2.08 \times 10^8$ | 1.69 | 4.41 | 3.83 |
| 82 | 0.5 | MAO | 15000 | 30 | 50 | $1.59 \times 10^8$ | 1.13 | 2.94 | 3.84 |
| 83 | 0.5 | MAO | 15000 | 30 | 80 | $1.27 \times 10^8$ | 1.47 | 4.78 | 3.08 |
| 84 | 5 | MMAO | 1500 | 15 | 25 | $6.30 \times 10^7$ | 1.32 | 2.31 | 5.72 |
| 85 | 1 | MMAO | 15000 | 30 | 25 | $1.24 \times 10^8$ | 0.85 | 1.96 | 4.36 |
| 86 | 0.5 | MMAO | 15000 | 30 | 25 | $8.20 \times 10^7$ | 1.05 | 2.18 | 4.82 |

EXAMPLE 87

The Polymerization of Ethylene Catalyzed by Complex 7

The operation process and the catalyst of the polymerizations were the same as those of Example 38. Except that 5.1 ml methyl aluminoxane (MAO) (1.46 mol/in toluene) and 0.5 µmol catalyst were employed, the other reaction conditions were the same as those of Example 38. 52.3 g polymer was obtained, and the polymerization activity was $2.09 \times 10^8$ g·mol$^{-1}$·h$^{-1}$. The weight-average molecular weight and number-average molecular weight of the obtained polymer was respectively Mw=$2.80 \times 10^5$ g·mol$^{-1}$ and Mn=$6.83 \times 10^4$ g·mol$^{-1}$, and PDI=4.10.

EXAMPLE 88

The Polymerization of Ethylene Catalyzed by Complex 7

The operation process and the catalyst of the polymerizations were the same as those of Example 38. Except that 5.1 ml modified methyl aluminoxane (MMAO) (1.90 mol/l in heptane) and 5 µmol catalyst were employed. The reaction lasted 5 min. The other reaction conditions were the same as those of Example 38. 37.2 g polymer was obtained, and the polymerization activity was $8.93 \times 10^7$ g·mol$^{-1}$·h$^{-1}$. The weight-average molecular weight and number-average molecular weight of the obtained polymer was respectively Mw=$11.90 \times 10^5$ g·mol$^{-1}$ and Mn=$3.15 \times 10^4$ g·mol$^{-1}$, and PDI=6.04.

EXAMPLE 89

The Polymerization of Ethylene Catalyzed by Complex 7

The operation process and used catalyst of the polymerizations were the same as those of Example 38. Except that 7.9 ml modified methyl aluminoxane (MMAO) (1.90 mol/l in heptane) was employed as promoter, the other reaction conditions were the same as those of Example 38. 68.53 g polymer was obtained, and the polymerization activity was $1.37 \times 10^8$ g·mol$^{-1}$·h$^{-1}$. The weight-average molecular weight and number-average molecular weight of the obtained polymer was respectively Mw=$1.04 \times 10^5$ g·mol$^{-1}$ and Mn=$2.24 \times 10^4$ g·mol$^{-1}$, and PDI=4.65.

EXAMPLE 90

The Polymerization of Ethylene Catalyzed by Complex 7

The operation process and the catalyst of the polymerizations were the same as those of Example 38. Except that 3.9 ml modified methyl aluminoxane (MMAO) (1.90 mol/l in heptane) and 0.5 µmol catalyst were employed, the other reaction conditions were the same as those of Example 38. 32.7 g polymer was obtained, and the polymerization activity was $1.3 \times 10^8$ g·mol$^{-1}$·h$^{-1}$. The weight-average molecular weight and number-average molecular weight of the obtained polymer was respectively Mw=$1.32 \times 10^5$ g·mol$^{-1}$ and Mn=$2.43 \times^4$ g·mol$^{-1}$, and PDI=5.43.

EXAMPLE 91

The Polymerization of Ethylene Catalyzed by Complex 7

The operation process and the catalyst of the polymerizations were the same as those of Example 51. Except that 5.1 ml methyl aluminoxane (MAO) (1.46 mol/l in toluene) and 5 µmol catalyst were employed, the other reaction conditions were the same as those of Example 51. 20.4 g polymer was obtained, and the polymerization activity was $4.90 \times 10^7$ g·mol$^{-1}$·h$^{-1}$. The weight-average molecular weight and number-average molecular weight of the obtained polymer was respectively Mw=$2.08 \times 10^5$ g·mol$^{-1}$ and Mn=$3.11 \times 10^4$ g·mol$^{-1}$, and PDI=6.68.

EXAMPLE 92

The Polymerization of Ethylene Catalyzed by Complex 20

0.5 µmol catalyst was employed for the polymerization of ethylene. The operation process and the catalyst of the polymerizations were the same as those of Example 89. 57.9 g polymer was obtained and the polymerization activity was $2.32 \times 10^8$ g·mol$^{-1}$·h$^{-1}$. The weight-average molecular weight and number-average molecular weight of the obtained polymer was respectively Mw=$1.84 \times 10^5$ g·mol$^{-1}$ and Mn=$4.03 \times 10^4$ g·mol$^{-1}$, and PDI=4.56.

EXAMPLE 93

The Polymerization of Ethylene Catalyzed by Complex 20

The operation process and used catalyst of the polymerizations were the same as those of Example 51. 3.9 ml modified methyl aluminoxane (MMAO) (1.90 mol/l in heptane) and 5 µmol catalyst were employed. The reaction lasted 15 min. The other reaction conditions were the same as those of Example 51. 77.0 g polymer was obtained, and the polymerization activity was $6.16 \times 10^7$ g·mol$^{-1}$. The weight-average molecular weight and number-average molecular weight of the obtained polymer was respectively Mw=$9.4 \times 10^4$ g·mol$^{-1}$ and Mn=$1.6 \times 10^4$ g·mol$^{-1}$, and PDI=5.91.

EXAMPLE 94

The Polymerization of Ethylene Catalyzed by Complex 20

The operation process and used catalyst of the polymerizations were the same as those of Example 51. 7.9 ml modified methyl aluminoxane (MMAO) (1.90 mol/l in heptane) was employed. The reaction lasted 25 min. The other reaction conditions were the same as those of Example 51. 64.3 g polymer was obtained, and the polymerization activity was $1.29 \times 10^8$ g·mol$^{-1}$·h$^{-1}$. The weight-average molecular weight and number-average molecular weight of the obtained polymer was respectively Mw=1.14×10$^5$ g·mol$^{-1}$ and Mn=2.09× 10$^4$ g·mol$^{-1}$, and PDI=5.46.

EXAMPLE 95

The Polymerization of Ethylene Catalyzed by Complex 20

The operation process and used catalyst of the polymerizations were the same as those of Example 51. 4 ml modified methyl aluminoxane (MMAO) (1.90 mol/l in heptane) and 0.5 μmmol catalyst were employed. The reaction lasted 25 min. The other reaction conditions were the same as those of Example 51. 31.9 g polymer was obtained, and the polymerization activity was 1.28×10$^8$ g·mol$^{-1}$·h$^{-1}$. The weight-average molecular weight and number-average molecular weight of the obtained polymer was respectively Mw=1.06× 10$^5$ g·mol$^{-1}$, and Mn=1.98×10$^4$ g·mol$^{-1}$, and PDI=5.35.

EXAMPLE 96

The Polymerization of Ethylene Catalyzed by Complex 20

The operation process and the catalyst of the polymerizations were the same as those of Example 51, except that the solution is 80 ml chlorobenzene. 7.9 ml modified methyl aluminoxane (MMAO) (1.90 mol/l in heptane) was employed. The reaction lasted 25 min. The other reaction conditions were the same as those of Example 51. 52.0 g polymer was obtained, and the polymerization activity was 1.04×10$^8$ g·mol$^{-1}$·h$^{-1}$. The weight-average molecular weight and number-average molecular weight of the obtained polymer was respectively Mw=0.50×10$^5$ g·mol$^{-1}$ and Mn=1.31× 10$^4$ g·mol$^{-1}$, and PDI=3.86.

EXAMPLE 97

The Polymerization of Ethylene Catalyzed by Complex 20

The operation process and the catalyst of the polymerizations were the same as those of Example 94, except that the solution is 80 ml n-heptane. 6.0 g polymer was obtained, and the polymerization activity was 1.20×10$^7$ g·mol$^{-1}$·h$^{-1}$. The weight-average molecular weight and number-average molecular weight of the obtained polymer was respectively Mw=4.75×10$^5$ g·mol$^{-1}$ and Mn=19.67×10$^4$ g·mol$^{-1}$, and PDI=2.41.

EXAMPLE 98

The Polymerization of Ethylene Catalyzed by Complex 20

The operation process and the catalyst of the polymerizations were the same as those of Example 94, except that the solution is 80 ml dichloromethane. 12.8 g polymer was obtained, and the polymerization activity was 2.56× 10$^7$ g·mol$^{-1}$·h$^{-1}$. The weight-average molecular weight and number-average molecular weight of the obtained polymer was respectively Mw=1.42×10$^5$ g·mol$^{-1}$ and Mn=1.33× 10$^4$ g·mol$^{-1}$, and PDI=10.73.

EXAMPLE 99

Cp$_2$ZrCl$_2$ Catalyzed the Polymerization of Ethylene 6.9 ml methyl aluminoxane (MAO) (1.46 mol/l in toluene) was employed as the catalyst promoter. The other reaction conditions were the same as those of Example 63. 18.7 g polymer was obtained, and the polymerization activity was 3.74×10$^7$ g·mol$^{-1}$·h$^{-1}$. The weight-average molecular weight and number-average molecular weight of the obtained polymer was respectively Mw=2.04×10$^5$ g·mol$^{-1}$ and Mn=9.23× 10$^4$ g·mol$^{-1}$, and PDI=2.21.

EXAMPLE 100

The Polymerization of Ethylene Catalyzed by Cp$_2$ZrCl$_2$ 14.0 ml methyl aluminoxane (MAO) (1.46 mol/l in toluene) was employed as the catalyst promoter. The other reaction conditions were the same as those of Example 63. 12.1 g polymer was obtained, and the polymerization activity was 2.42×10$^7$ g·mol$^{-1}$·h$^{-1}$. The weight-average molecular weight and number-average molecular weight of the obtained polymer was respectively Mw=1.40×10$^5$ g·mol$^{-1}$ and Mn=6.92× 10$^4$ g·mol$^{-1}$, and PDI=2.02.

EXAMPLE 101

The Polymerization of Ethylene Catalyzed by Cp$_2$ZrCl$_2$

The amount of the complex is 0.5 μmol 5.0 ml methyl aluminoxane (MAO) (1.46 mol/l in toluene) was employed as the catalyst promoter. The other reaction conditions were the same as those of Example 63. 7.6 g polymer was obtained, and the polymerization activity was 3.04×10$^7$ g·mol$^{-1}$·h$^{-1}$. The weight-average molecular weight and number-average molecular weight of the obtained polymer was respectively Mw=1.72×10$^5$ g·mol$^{-1}$ and Mn=7.22×10$^4$ g·mol$^{-1}$, and PDI=2.38.

EXAMPLE 102

The Polymerization of Ethylene Catalyzed by Cp$_2$ZrCl$_2$ 6.5 ml modified methyl aluminoxane (MMAO) (1.90 mol/l in toluene) was employed as the catalyst promoter. The other reaction conditions were the same as those of Example 63. 8.12 g polymer was obtained, and the polymerization activity was 1.62×10$^7$ g·mol$^{-1}$·h$^{-1}$. The weight-average molecular weight and number-average molecular weight of the obtained polymer was respectively Mw=1.05×10$^5$ g·mol$^{-1}$ and Mn=5.40×10$^4$ g·mol$^{-1}$, and PDI=1.94.

EXAMPLE 103

The Polymerization of Ethylene Catalyzed by Cp$_2$ZrCl$_2$

The amount of the complex is 0.5 μmol. 3.9 ml modified methyl aluminoxane (MMAO) (1.90 mol/l in toluene) was employed as the catalyst promoter. The other reaction conditions were the same as those of Example 63. 8.50 g polymer was obtained, and the polymerization activity was 3.40× 10$^7$ g·mol$^{-1}$·h$^{-1}$. The weight-average molecular weight and number-average molecular weight of the obtained polymer was respectively Mw=1.03×10$^5$ g·mol$^{-1}$ and Mn=4.88×10$^4$ g·mol$^{-1}$, and PDI=2.11.

EXAMPLE 104

The Copolymerization of Ethylene and Norborene Catalyzed by Complex 6

2.5 μmol catalyst 6 was dissolved with 20 ml toluene to form a solution and 5.1 ml methyl aluminoxane (MAO) (1.46 mol/l in toluene) was added into the solution so as to make Al/Zr equal to 3000 to form a catalyst solution 60 ml toluene, 15 ml 6.71M norborene in toluene solution and the catalyst solution were added into a 500 ml stainless steel autoclave, and the concentration of norborene reached 1M. Mechanical stirring was begun and kept at 200 rpm. When the polymerization temperature reached 20° C., ethylene was filled into the autoclave. The ethylene pressure was kept at 1 MPa, and the reaction was stirred for 30 min to obtain a polymer. The polymer was washed with ethanol solution acidified by 5% hydrochloric acid and dried in a drying vacuum oven at 60° C. to constant weight. 0.0365 g polymer was obtained and the polymerization activity was 2.92×10$^4$ g·mol$^{-1}$·h$^{-1}$.

EXAMPLE 105

The Copolymerization of Ethylene and Norborene Catalyzed by Complex 6

The operation process and the catalyst of polymerization were the same as those of Example 104. Except that the polymerization temperature was 80° C., the other reaction conditions were the same as those of Example 104. 2.504 g polymer was obtained and the polymerization activity was 2.00×10$^6$ g·mol$^{-1}$·h$^{-1}$.

EXAMPLE 106

The Copolymerization of Ethylene and Norborene Catalyzed by Complex 6

The operation process and the catalyst of polymerization were the same as those of Example 105. Except that the concentration of norborene reached 0.5M, the other reaction conditions were the same as those of Example 105. 8.3838 g polymer was obtained and the polymerization activity was 6.71×10$^6$ g·mol$^{-1}$·h$^{-1}$.

EXAMPLE 107

The Copolymerization of Ethylene and Norborene Catalyzed by Complex 6

The operation process and the catalyst of polymerization were the same as those of Example 105. Except that the concentration of norborene reached 0.5M, the other reaction conditions were the same as those of Example 105. 0.1470 g polymer was obtained and the polymerization activity was 1.18×10$^5$ g·mol$^{-1}$·h$^{-1}$.

EXAMPLE 108

The Copolymerization of Ethylene and Norborene Catalyzed by Complex 6

The operation process and the catalyst of polymerization were the same as those of Example 105. 1 μmol catalyst 6 was dissolved with 20 ml toluene to form a solution and 10.2 ml methyl aluminoxane (MAO) (1.46 mol/l in toluene) was added into the solution so as to make Al/Zr equal to 15000. The ethylene pressure was kept at 3 MPa, and the other reaction conditions were the same as those of Example 105. 63.4 g polymer was obtained and the polymerization activity was 1.27×10$^8$ g·mol$^{-1}$·h$^{-1}$. The weight-average molecular weight and number-average molecular weight of the obtained polymer was respectively Mw=4.34×10$^4$ g·mol$^{-1}$ and Mn=1.33×10$^4$ g·mol$^{-1}$, and PDI=3.27.

EXAMPLE 109

The Copolymerization of Ethylene and Norborene Catalyzed by Complex 6

The operation process and the catalyst of polymerization were the same as those of Example 108. The concentration of norborene reached 0.5M. The other reaction conditions were the same as those of Example 108. 63.4 g polymer was obtained and the polymerization activity was 1.27×10$^8$ g·mol$^{-1}$·h$^{-1}$.

EXAMPLE 110

The Copolymerization of Ethylene and Norborene Catalyzed by Complex 6

The operation process and the catalyst of polymerization were the same as those of Example 108. The concentration of norborene reached 0.3M. The other reaction conditions were the same as those of Example 108. 75.0 g polymer was obtained and the polymerization activity was 1.50×10$^8$ g·mol$^{-1}$·h$^{-1}$. The weight-average molecular weight and number-average molecular weight of the obtained polymer were respectively Mw=6.35×10$^4$ g·mol$^{-1}$ and Mn=2.12×10$^4$ g·mol$^{-1}$, and PDI=2.99.

EXAMPLE 111

The Copolymerization of Ethylene and Norborene Catalyzed by Complex 6

The operation process and the catalyst of polymerization were the same as those of Example 108. The concentration of norborene reached 0.1M. The other reaction conditions were the same as those of Example 108. 62.7 g polymer was obtained and the polymerization activity was 1.25×10$^8$ g·mol$^{-1}$·h$^{-1}$. The weight-average molecular weight and number-average molecular weight of the obtained polymer were respectively Mw=5.80×10$^4$ g·mol$^{-1}$ and Mn=2.02×10$^4$ g·mol$^{-1}$, and PDI=2.88.

EXAMPLE 112

The Copolymerization of Ethylene and 1-Hexene Catalyzed by Complex 6

2.5% mol catalyst 6 was dissolved with 20 ml toluene to form a solution, and 5.1 ml methyl aluminoxane (MAO) (1.46 mol/l in toluene) was added into the solution so as to make Al/Zr equal to 3000 to form a catalyst solution 63 ml toluene, 12.4 ml 1-butylethylene and the catalyst solution were added into a 500 ml stainless steel autoclave, and the concentration of 1-hexene reached 1M. Mechanical stirring was begun and kept at 200 rpm. When the polymerization temperature reached 20° C., ethylene was filled into the autoclave. The ethylene pressure was kept at 1 MPa, and the reaction was stirred for 30 min to obtain a polymer. The polymer was washed with ethanol solution acidified by 5% hydrochloric acid and dried in a drying vacuum oven at 60° C. to constant weight. 3.70 g polymer was obtained and the polymerization activity was $2.96 \times 10^6$ g·mol$^{-1}$·h$^{-1}$.

EXAMPLE 113

The Copolymerization of Ethylene and 1-Hexene Catalyzed by Complex 6

The operation process and the catalyst of polymerization were the same as those of Example 112. Except that the polymerization temperature was 80° C., the other reaction conditions were the same as those of Example 112. 15.765 g polymer was obtained and the polymerization activity was $1.26 \times 10^7$ g.mol$^{-1}$.h$^{-1}$.

EXAMPLE 114

The Copolymerization of Ethylene and 1-Hexene Catalyzed by Complex 6

The operation process and the catalyst of polymerization were the same as those of Example 113. 1 μmol catalyst 6 was dissolved with 20 ml toluene to form a solution, and 10.2 ml methyl aluminoxane (MAO) (1.46 mol/l in toluene) was added into the solution so as to make Al/Zr equal to 15000. The ethylene pressure was kept at 3 MPa, and the other reaction conditions were the same as those of Example 113. 57.6 g polymer was obtained and the polymerization activity was $1.15 \times 10^8$ g.mol$^{-1}$.h$^{-1}$. The weight-average molecular weight and number-average molecular weight of the obtained polymer were respectively Mw=$1.89 \times 10^4$ g.mol$^{-1}$ and Mn=$0.47 \times 10^4$ g.mol$^{-1}$, and PDI=4.00.

EXAMPLE 115

The Copolymerization of Ethylene and 1-Hexene Catalyzed by Complex 6

The operation process and the catalyst of polymerization were the same as those of Example 114. Except that the polymerization temperature was 50° C., the other reaction conditions were the same as those of Example 114. 56.9 g polymer was obtained and the polymerization activity was $1.14 \times 10^7$ g.mol$^{-1}$.h$^{-1}$.

EXAMPLE 116

The Copolymerization of Ethylene and 1-Hexene Catalyzed by Complex 6

The operation process and the catalyst of polymerization were the same as those of Example 115. Except that the polymerization temperature was 20° C., the other reaction conditions were the same as those of Example 115. 2.1 g polymer was obtained and the polymerization activity was $4.20 \times 10^6$ g.mol$^{-1}$.h$^{-1}$.

EXAMPLE 117

The Copolymerization of Ethylene and 1-Hexene Catalyzed by Complex 6

The operation process and the catalyst of polymerization were the same as those of Example 114. Except that the concentration of 1-hexene reached 1.5M, the other reaction conditions were the same as those of Example 114. 56.0 g polymer was obtained and the polymerization activity was $1.12 \times 10^8$ g.mol$^{-1}$.h$^{-1}$.

EXAMPLE 118

The Copolymerization of Ethylene and 1-Hexene Catalyzed by Complex 6

The operation process and the catalyst of polymerization were the same as those of Example 117. Except that the concentration of 1-hexene reached 0.5M, the other reaction conditions were the same as those of Example 117. 57.9 g polymer was obtained and the polymerization activity was $1.16 \times 10^8$ g.mol$^{-1}$.h$^{-1}$.

EXAMPLE 119

The Copolymerization of Ethylene and 1-Hexene Catalyzed by Complex 6

The operation process and the catalyst of polymerization were the same as those of Example 118. Except that the concentration of 1-hexene reached 0.3M, the other reaction conditions were the same as those of Example 118. 56.6 g polymer was obtained and the polymerization activity was $1.13 \times 10^8$ g.mol$^{-1}$.h$^{-1}$. The weight-average molecular weight and number-average molecular weight of the obtained polymer were respectively Mw=$4.83 \times 10^4$ g.mol$^{-1}$ and Mn=$1.60 \times 10^4$ g.mol$^{-1}$, and PDI=3.02.

EXAMPLE 120

The Copolymerization of Ethylene and 1-Hexene Catalyzed by Complex 6

The operation process and the catalyst of polymerization were the same as those of Example 119. Except that the concentration of 1-hexene reached 0.1M, the other reaction conditions were the same as those of Example 119. 52.3 g polymer was obtained and the polymerization activity was $1.05 \times 10^8$ g.mol$^{-1}$.h$^{-1}$. The weight-average molecular weight and number-average molecular weight of the obtained polymer were respectively Mw=$4.87 \times 10^4$ g.mol$^{-1}$ and Mn=$1.51 \times 10^4$ g.mol$^{-1}$, and PDI=3.22.

EXAMPLE 121

The Copolymerization of Ethylene and 1-Octene Catalyzed by Complex 6

2.5 μmol catalyst 6 was dissolved with 20 ml toluene to form a solution, and 5.1 ml methyl aluminoxane (MAO) (1.46 mol/l in toluene) was added into the solution so as to make Al/Zr equal to 3000 to form a catalyst solution. 60 ml toluene, 15.7 ml 1-octylene and the catalyst solution were added into a 500 ml stainless steel autoclave, and the concentration of 1-octylene reached 1M. Mechanical stirring was begun and kept at 200 rpm. When the polymerization temperature reached 20° C., ethylene was filled into the autoclave. The ethylene pressure was kept at 1 MPa, and the reaction was stirred for 30 min to obtain a polymer. The polymer was washed with ethanol solution acidified by 5% hydrochloric acid and dried in a drying vacuum oven at 60° C. to constant weight. 2.048 g polymer was obtained and the polymerization activity was $1.64 \times 10^6$ g·mol$^{-1}$·h$^{-1}$.

EXAMPLE 122

The Copolymerization of Ethylene and 1-Octene Catalyzed by Complex 6

The operation process and the catalyst of polymerization were the same as those of Example 121. Except that the polymerization temperature was 80° C., the other reaction conditions were the same as those of Example 121. 21.45 g polymer was obtained and the polymerization activity was $1.72 \times 10^7$ g.mol$^{-1}$.h$^{-1}$.

EXAMPLE 123

The Copolymerization of Ethylene and 1-Octene Catalyzed by Complex 6

The operation process and the catalyst of polymerization were the same as those of Example 122. 1 µmol catalyst 6 was dissolved with 20 ml toluene to form a solution, and 10.2 ml methyl aluminoxane (MAO) (1.46 mol/l in toluene) was added into the solution so as to make Al/Zr equal to 15000. The ethylene pressure was kept at 3 MPa, and the other reaction conditions were the same as those of Example 122. 58.8 g polymer was obtained and the polymerization activity was $1.18 \times 10^7$ g.mol$^{-1}$.h$^{-1}$. The weight-average molecular weight and number-average molecular weight of the obtained polymer was respectively Mw=$2.42 \times 10^4$ g.mol$^{-1}$ and Mn=$0.53 \times 10^4$ g.mol$^{-1}$, and PDI=4.60.

EXAMPLE 124

The Copolymerization of Ethylene and 1-Octene Catalyzed by Complex 6

The operation process and the catalyst of polymerization were the same as those of Example 123. Except that the concentration of 1-octene reached 0.5M, the other reaction conditions were the same as those of Example 123. 63.4 g polymer was obtained and the polymerization activity was $1.27 \times 10^8$ g.mol$^{-1}$.h$^{-1}$.

EXAMPLE 125

The Copolymerization of Ethylene and 1-Octene Catalyzed by Complex 6

The operation process and the catalyst of polymerization were the same as those of Example 124. Except that the concentration of 1-octene reached 0.3M, the other reaction conditions were the same as those of Example 124. 64.3 g polymer was obtained and the polymerization activity was $1.28 \times 10^8$ g.mol$^{-1}$.h$^{-1}$. The weight-average molecular weight and number-average molecular weight of the obtained polymer were respectively Mw=$5.36 \times 10^4$ g.mol$^{-1}$ and Mn=$1.61 \times 4$ g.mol$^{-1}$, and PDI=3.32.

EXAMPLE 126

The Copolymerization of Ethylene and 1-Octene Catalyzed by Complex 6

The operation process and the catalyst of polymerization were the same as those of Example 125. Except that the concentration of 1-octene reached 0.1M, the other reaction conditions were the same as those of Example 125. 59.3 g polymer was obtained and the polymerization activity was $1.19 \times 10^8$ g.mol$^{-1}$.h$^{-1}$. The weight-average molecular weight and number-average molecular weight of the obtained polymer were respectively Mw=$5.09 \times 10^4$ g.mol$^{-1}$ and Mn=$1.84 \times 10^4$ g.mol$^{-1}$, and PDI=2.76.

What is claimed is:

1. A phosphine-substituted vinyl containing metallocene catalyst, having the following general formula:

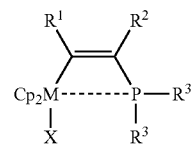

characterized in that Cp is a ligand containing cyclopentadiene having 1~5 substitutions, of which two neighbors connecting to each other to form fused rings having more than two members; $R^1$-$R^3$ are selected from the groups consisting of hydrogen, $C_1$~$C_{18}$ alkyl or perfluoro-alkyl, $C_6$~$C_{24}$ aralkyl or alkaryl, or phenyl; $R_3$ is further selected from the group consisting of cyclohexyl; X is selected from the groups consisting of $C_1$~$C_6$ alkyl or benzyl; M is selected from the groups consisting of titanium or zirconium.

2. The phosphine-substituted vinyl containing metallocene catalyst according to claim 1, characterized in that $R^1$ and $R^2$ are selected from the groups consisting of ethyl, propyl, butyl, phenyl or para-methyl phenyl; $R^3$ is selected from the groups consisting of phenyl, methyl, isopropyl or cyclohexyl.

3. The phosphine-substituted vinyl containing metallocene catalyst according to claim 1, characterized in that Cp is mono- or poly-substituted groups by cyclopentadienyl, indenyl or flourenyl; $R^1$-$R^3$ is $C_1$~$C_{18}$ alkyl or perfluoro-alkyl.

4. A process for preparation of the phosphine-substituted vinyl containing metallocene catalyst according to claim 1, comprising the steps of:

(1) Adding a dihalide dicyclopentadienyl metallic compound into a solvent and then the first strong alkaline compound to form a first mixture; wherein the amount of the solvent is 10~20 times the weight of the dihalide dicyclopentadienyl metallic compound; the first strong alkaline compound and the dihalide dicyclopentadienyl metallic compound are in the proportion of 1.2:2 by weight;

(2) Adding the second alkaline compound into the first mixture and then an alkyne compound to form the second mixture; wherein the alkyne compound, the first and second alkaline compounds, and the dihalide dicyclopentadienyl metallic compound are in the proportion of 1:2:1.2 by weight;

(3) Adding dialkyl phosphorus halide into the second mixture and then 3M dilute hydrochloric acid to get the coarse products; wherein the dialkyl phosphorus halide and the dihalide dicyclopentadienyl metallic compound are in the proportion of 1:1.2 by weight.

5. The process for preparation of the phosphine-substituted vinyl containing metallocene catalyst according to claim 4, characterized in that the metal in the dihalide dicyclopentadienyl metallic compound is titanium, zirconium or celtium.

6. The process for preparation of the phosphine-substituted vinyl containing metallocene catalyst according to claim 4, characterized in that the first strong alkaline compound is selected from the groups consisting of alkylates or hydrides of alkali metals or alkyl magnesium bromide.

7. The process for preparation of the phosphine-substituted vinyl containing metallocene catalyst according to claim 4, characterized in that the solvent is diethyl ether or tetrahydrofuran.

8. The process for preparation of the phosphine-substituted vinyl containing metallocene catalyst according to claim 4, characterized in that the second alkaline compound is tri-substituted organic amine or pyridines compounds.

9. The process for preparation of the phosphine-substituted vinyl containing metallocene catalyst according to claim 4, characterized in that the alkyne compound is $C_2$~$C_{24}$ ethyne compound.

10. The process for preparation of the phosphine-substituted vinyl containing metallocene catalyst according to claim 4, characterized in that the general formula of the dialkyl phosphorus halide compound is $XPR_2$, wherein X is a halogen and R is hydrocarbonyl.

11. The process for preparation of the phosphine-substituted vinyl containing metallocene catalyst according to claim 6, characterized in that in the alkylates of the alkali metal, the alkali metal is lithium, sodium or potassium, and the alkyl is methyl, ethyl or butyl.

12. The process for preparation of the phosphine-substituted vinyl containing metallocene catalyst according to claim 6, characterized in that the alkyl in the alkyl magnesium bromide is $C_1$~$C_8$ alkyl or $C_6$~$C_{18}$ aralkyl.

13. The process for preparation of the phosphine-substituted vinyl containing metallocene catalyst according to claim 8, characterized in that said second alkaline compound is N, N-dimethyl-4-methylaminopyridine.

14. The process for preparation of the phosphine-substituted vinyl containing metallocene catalyst according to claim 9, characterized in that $C_2$~$C_{24}$ ethyne compound is 2-crotonylene, 3-hexyne, 4-octyne, 5-decyne, 1-phenyl allylene; 1-phenyl valerylene, 1,2-diphenylacetylene; 1,2-dinaphthylacetylene, 1,2-di(para-chlorophenyl)acetylene; 1,2-di(o-chlorophenyl)acetylene.

15. The process for preparation of the phosphine-substituted vinyl containing metallocene catalyst according to claim 10, characterized in that in the general formula $XPR_2$, X is selected from the groups consisting of Cl and Br; R is selected from the groups consisting of derivatives of alkyl or aryl, or halogen-substituted derivatives of alkyl or aryl.

16. A process for using a phosphine-substituted vinyl containing metallocene catalyst comprising:
providing a phosphine-substituted vinyl containing metallocene catalyst as a polymerization catalyst, the phosphine-substituted vinyl containing metallocene catalyst having the following general formula

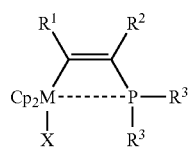

characterized in that Cp is a ligand containing cyclopentadiene having 1~5 substitutions, of which two neighbors connecting to each other to form fused rings having more than two members; $R^1$-$R^3$ is selected from the groups consisting of hydrogen, $C_1$~$C_{18}$ alkyl or perfluoro-alkyl, $C_6$~$C_{24}$ aralkyl or alkaryl; M is selected from the groups consisting of metals of the IVB group; and X is selected from the groups consisting of halogens, $C_1$~$C_{24}$ alkyl, alkoxyl, silicone or alkaryl; and
polymerizing a monomer alpha-olefin using the polymerization catalyst.

17. The process for using the phosphine-substituted vinyl containing metallocene catalyst according to claim 16, characterized in that aluminoxane or modified aluminoxane, aluminum alkyl, halogenated aluminum alkyl or the mixture thereof is employed as a catalyst promoter.

18. The process for using the phosphine-substituted vinyl containing metallocene catalyst according to claim 16, characterized in that the monomer alpha-olefin is selected from the groups consisting of $C_2$~$C_{24}$ olefin including ethylene, propylene, 1-butylene, 1-hexylene, 1-caprylene, 1-decylene, 1-dodecylene, 1-tetradecene, norborene, styrene or mixture of any two of them.

19. The process for using the phosphine-substituted vinyl containing metallocene catalyst according to claim 17, characterized in that the molar ratio of metallicum alumina in the catalyst promoter and the central metal in the polymerization catalyst is 10~50000.

20. The process for using the phosphine-substituted vinyl containing metallocene catalyst according to claim 17, characterized in that said aluminoxane is methyl aluminoxane, ethyl aluminoxane or isobutyl aluminoxane; aluminum alkyl is trimethyl aluminum, triethyl aluminum, triisobutyl aluminum or triorthohexyl aluminum; halogenated aluminum alkyl is diethyl aluminium chloride, sesquiethyl aluminum chloride or ethyl aluminium dichloride; the mixture includes the mixture of methyl aluminoxane and aluminum alkyl.

21. The process for using the phosphine-substituted vinyl containing metallocene catalyst according to claim 16, characterized in that the temperature of polymerization is 0~150° C.

22. The process for using the phosphine-substituted vinyl containing metallocene catalyst according to claim 16, characterized in that the pressure of polymerization is 0.01~10.0 MPa.

23. The process for using the phosphine-substituted vinyl containing metallocene catalyst according to claim 16, characterized in that the amount of comonomer for polymerization and catalyst is in the volume ratio of 1000~1000000.

24. The process for using the phosphine-substituted vinyl containing metallocene catalyst according to claim 21, characterized in that the temperature of polymerization is 20~120° C.

25. The process for using the phosphine-substituted vinyl containing metallocene catalyst according to claim 22, characterized in that the pressure of polymerization is 0.1~5 MPa.

26. The process for using the phosphine-substituted vinyl containing metallocene catalyst according to claim 23, characterized in that the molar ratio of metallic aluminum in the catalyst promoter and the central metal in the polymerization catalyst is 200~20000.

* * * * *